United States Patent
Lee et al.

(10) Patent No.: US 7,855,069 B2
(45) Date of Patent: Dec. 21, 2010

(54) METHOD AND APPARATUS FOR THE RAPID DISRUPTION OF CELLS OR VIRUSES USING MICRO MAGNETIC BEADS AND LASER

(75) Inventors: Jeong-gun Lee, Seoul (KR); Young-nam Kwon, Gyeonggi-do (KR); Young-a Kim, Gyeonggi-do (KR); Myo-yong Lee, Gyeonggi-do (KR); Shin-i Yoo, Gyeonggi-do (KR); Yeon-ja Cho, Seoul (KR); Kwang-ho Cheong, Palo Alto, CA (US); Chang-eun Yoo, Seoul (KR); Seung-yeon Yang, Gyeonggi-do (KR)

(73) Assignee: Samsung Electronics Co., Ltd. (KR)

( * ) Notice: Subject to any disclaimer, the term of this patent is extended or adjusted under 35 U.S.C. 154(b) by 397 days.

(21) Appl. No.: 11/253,541

(22) Filed: Oct. 19, 2005

(65) Prior Publication Data
US 2006/0084165 A1 Apr. 20, 2006

(30) Foreign Application Priority Data

Oct. 19, 2004 (KR) ............ 10-2004-0083586
May 10, 2005 (KR) ............ 10-2005-0038988
Aug. 26, 2005 (KR) ............ 10-2005-0078886

(51) Int. Cl.
C12M 1/42 (2006.01)
C12M 1/33 (2006.01)

(52) U.S. Cl. ............ 435/287.2; 435/288.5; 435/288.7; 435/306.1

(58) Field of Classification Search ............ 435/306.1
See application file for complete search history.

(56) References Cited

U.S. PATENT DOCUMENTS 5,234,809 A 8/1993 Boom et al.

(Continued)

FOREIGN PATENT DOCUMENTS

EP 1655366 A2 5/2006

(Continued)

OTHER PUBLICATIONS

Deggerdal, Arne and Larsen, Frank, "Rapid Isolation of PCR-Ready DNA from Blood, Bone Marrow and Cultured Cells, Based on Paramagnetic Beads," *Bio Techniques* (1997) 22(3): 554-557.

(Continued)

*Primary Examiner*—William H Beisner
(74) *Attorney, Agent, or Firm*—Cantor Colburn LLP

(57) ABSTRACT

A method and apparatus for a rapid disruption of cells or viruses using micro magnetic beads and a laser are provided. According to the method and apparatus for a rapid disruption of cells or viruses using micro magnetic beads and a laser, cell lysis within 40 seconds is possible, the apparatus can be miniaturized using a laser diode, a DNA purification step can be directly performed after a disruption of cells or viruses, and a solution containing DNA can be transferred to a subsequent step after cell debris and beads to which inhibitors of a subsequent reaction are attached are removed with an electromagnet. In addition, by means of the cell lysis chip, an evaporation problem is solved, vibrations can be efficiently transferred to cells through magnetic beads, a microfluidics problem on a rough surface is solved by hydrophobically treating the inner surface of the chip, and the cell lysis chip can be applied to LOC.

14 Claims, 25 Drawing Sheets

U.S. PATENT DOCUMENTS

| | | | |
|---|---|---|---|
| 5,403,710 | A | 4/1995 | Weisburg et al. |
| 5,705,628 | A | 1/1998 | Hawkins |
| 5,863,502 | A * | 1/1999 | Southgate et al. ............. 422/58 |
| 6,043,080 | A * | 3/2000 | Lipshutz et al. .......... 435/287.2 |
| 6,156,576 | A | 12/2000 | Allbritton et al. ............. 436/63 |
| 6,335,201 | B1 | 1/2002 | Allbritton et al. |
| 6,613,525 | B2 * | 9/2003 | Nelson et al. ................... 435/6 |
| 6,685,730 | B2 | 2/2004 | West et al. |
| 6,783,736 | B1 * | 8/2004 | Taylor et al. ................ 422/103 |
| 6,914,137 | B2 * | 7/2005 | Baker ........................ 536/25.4 |
| 7,192,560 | B2 | 3/2007 | Parthasarathy et al. |
| 2003/0095897 | A1 | 5/2003 | Grate et al. |
| 2003/0096429 | A1 * | 5/2003 | Baeumner et al. ........... 436/174 |
| 2006/0094051 | A1 | 5/2006 | Lee et al. |
| 2006/0110725 | A1 | 5/2006 | Lee et al. |
| 2006/0188876 | A1 | 8/2006 | Kilaas et al. |

FOREIGN PATENT DOCUMENTS

| | | | |
|---|---|---|---|
| JP | 2000-029541 A | 1/2000 | |
| JP | 2004-049105 A | 2/2004 | |
| WO | 9945372 A1 | 9/1999 | |
| WO | 0073412 A2 | 12/2000 | |

OTHER PUBLICATIONS

Li, Huaina et al, "Spatial Control of Cellular Measurements with the Laser Micropipet," *Anal. Chem.* (2001) 73: 4625-4631.

Rudi, K. et al., "Rapid, Universal Method of Isolate PCR-Ready DNA Using Magnetic Beads," *BioTechniques*, (1997) 22: 506-511.

Taylor, Michael T. et al., "Lysing Bacterial Spores by Sonication through a Flexible Interface in a Microfluidic System," *Anal. Chem.* (2001) 73: 492-496.

European Search Report; Application No. EP 05 02 2672; Date; Jun. 14, 2006.

"Self Contained, Fully Integrated Biochip for Sample Preparation, Polymerase Chain Reaction Amplification, and DNA Microarray Detection"; Authors: Robin Hui Liu, Jianing Yang, Ralf Lenigk, Justin Bonanno, and Piotr Grodzinski; Analytical Chemistry, vol. 76, No. 7, Apr. 1, 2004; 1824-1831 XP-001196720.

"Recent Developments of Magnetic Beads for Use in Nucleic Acid Purification"; Authors: Peter R. Levison, Stephen E. Bader, Jon Dennis, Prit Hathi, Martin J. Davies, Ian J. Bruce, Dieter Schimkat; Journal of Chromatography A. 816 (1998) 107-111.

"Quantitative Cell Lysis of Indigenous Microorganisms and Rapid Extraction of Microbial DNA From Sediment"; Authors: Margaret I. More, James B. Herrick, Margarida C. Silva, William C. Ghiorse and Eugene L. Madsen; Applied and Environmental Microbiology, May 1994, p. 1572-1580; XP 000574303.

"Laser Based Disruption of *Bacillus* Spores on a Microchip"; Authors: Oliver Hofmann, Kirk Murray, Alan-Shaun Wilkinson, Timothy Cox, Andreas Manz; 8th International Conference on Miniaturized Systems for chemistry and Life Sciences; Sep. 26-30, 2004, XP009066976.

Elgort, M.G., et al.; "Extraction and Amplification of Genomic DNA from Human Blood on Nanoporous Aluminum Oxide Membranes"; Clinical Chemistry; vol. 50, No. 10; pp. 1817-1819; 2004.

Li, H., et al.; "Selective genotyping of individual cells by capillary polymerase chain reaction"; Electrophoresis; vol. 23; pp. 3372-3380; 2002.

Tian, H., et al.; "Evaluation of Silica Resins for Direct and Efficient Extraction of DNA from Complex Biological Matrices in a Miniaturized Format"; Analytical Biochemistry; vol. 283; pp. 175-191; 2000.

Safarik, I., et al.; "Biologically Active Compounds and Xenobiotics: Magnetic Affinity Separations"; Encyclopedia of Separation Science, Academic Press; pp. 2163-2170; 2000.

Leszczynski D. et al, Laser-beam-triggered Microcavitation: a novel method for selective cell destruction, Radiation Res. 2001; 156: 399-407.

\* cited by examiner (A)  (B)  (C)

M  1  2  3  4  5

METHOD AND APPARATUS FOR THE RAPID DISRUPTION OF CELLS OR VIRUSES USING MICRO MAGNETIC BEADS AND LASER

CROSS-REFERENCE TO RELATED PATENT APPLICATION

This application claims the benefit of Korean Patent Application No. 10-2004-0083586, filed on Oct. 19, 2004, Korean Patent Application No. 10-2005-0038988, filed on May 10, 2005, and Korean Patent Application No. 10-2005-0078886, filed on Aug. 26, 2005, in the Korean Intellectual Property Office, the disclosures of which are incorporated herein in their entirety by reference.

BACKGROUND OF THE INVENTION

1. Field of the Invention

The present invention relates to a method and apparatus for a rapid disruption of cells or viruses using micro magnetic beads and a laser.

2. Description of the Related Art

Generally, a molecular diagnosis of a specific pathogenic bacteria is performed in four steps: 1) cell lysis, 2) DNA isolation, 3) DNA amplification and 4) DNA detection.

An efficient extraction of DNA from a cell is required in many applications and is essential in the molecular diagnosis, in particular, an identification and quantification of a pathogenic bacteria. The molecular diagnosis is generally performed by DNA amplification after DNA extraction. The DNA amplification includes a polymerase chain reaction (PCR), a ligase chain reaction, a stranded-displacement amplification, a nucleic acid-based amplification, a repair chain reaction, a helicase chain reaction, a QB replicase amplification, an a ligation activated transcription.

A method of isolating DNA from a cell is performed using materials having a tendency of bonding to DNA. Examples of the materials for DNA separation include silica, glass fiber, anion exchange resin and magnetic beads (Rudi, K. et al., *Biotechniqures* 22, 506-511 (1997); and Deggerdal, A. et al., *Biotechniqures* 22, 554-557 (1997)). To avoid manual steps and to remove operator error, several automatic machines are developed for high-throughput DNA extractions.

Cell lysis is conventionally performed by a mechanical, chemical, thermal, electrical, ultrasonic or microwave method (Michael T. Taylor et al., *Anal. Chem.*, 73, 492-496 (2001)).

A chemical method includes the use of lyzing agents for disrupting cells to release DNA. An additional treatment of cell extracts with a chaotropic reagent is necessary to denature proteins. The chemical lysis method is disadvantageous in that harsh chemicals are used to disrupt the cells. Since they can interfere with the subsequent PCR, it is necessary to purify the DNA prior to the PCR. The chemical method is labor-intensive and time-consuming, requires expensive consumables and has often a low DNA yield. A thermal method involves cycles of freezing/thawing, but cannot often disrupt many structures within cells.

Heating is an alternative method of disrupting cell walls or membranes. Simple heating is disadvantageous in that it results in the denaturation of proteins, which can be attached to released DNA. They can also interfere with DNA amplification. A physical method uses a bulky and expensive pressure apparatus, which is not suitable for a Lab-on-a-Chip (LOC) application.

An ultrasonic treatment is an alternative of the physical method, wherein a cell solution or suspension is placed in a chamber located in an ultrasonic bath. Ultrasonic disruption has many disadvantages in cell lysis. First, a distribution of ultrasonic energy is not uniform. The nonuniform distribution of ultrasonic energy leads to inconsistent results. Second, due to the energy divergence in the ultrasonic bath, it takes often several minutes to completely disrupt cells. Lastly, the ultrasonic method generates unpleasant sounds.

A laser has many advantages in the disruption of cells and can be readily applied to LOC (Huaina Li et al., *Anal Chem*, 73, 4625-4631 (2001)).

U.S. Patent Publication No. 2003/96429 A1 discloses a laser-induced cell lysis system. When only a laser is used, an efficient cell lysis does not occur. As a result of performing an experiment using *E. coli* placed in a very clear solution, it is confirmed that when irradiating only a laser, a low cell lysis efficiency is obtained. A concentration of DNA measured after irradiating a laser for 150 seconds is 3.77 ng/μl because laser energy is not effectively transferred to cells. A concentration of DNA measured after boiling cells at 95° C. for 5 minutes by means of a conventional heating method is 6.15 ng/μl.

U.S. Pat. No. 6,685,730 discloses optically-absorbing nanoparticles for enhanced tissue repair. This patent includes a method of joining tissue comprising: delivering nanoparticles having dimensions of from 1 to 1000 nanometers that absorb light at one or more wavelengths to the tissue to be joined; and exposing said nanoparticles to light at one or more wavelengths that are absorbed by the nanoparticles. This method causes only a loss of function of the cells by using a laser and nanoparticles and there is no description of a method of disrupting cells by vibrating a solution containing cells and particles.

Thus, the inventors intensively studied in order to overcome the above problems and discovered that cells or viruses can be rapidly disrupted when vibrating a solution containing them using micro magnetic beads and a laser.

SUMMARY OF THE INVENTION

The present invention provides a method of disrupting cells or viruses, the method including: adding magnetic beads to a solution containing cells or viruses; vibrating the magnetic beads; and irradiating a laser to the magnetic beads to disrupt the cells or viruses.

The present invention also provides an apparatus for the disruption of cells or viruses including: a cell lysis chamber having an inlet hole through which a sample and magnetic beads are introduced; a vibrator attached to the chamber and mixing the sample and the magnetic beads in the chamber; and a laser generator attached to the chamber and supplying a laser.

The present invention also provides an apparatus for the disruption of cells or viruses, including: a cell lysis chip having an inlet hole through which a sample and magnetic beads are introduced; a vibrator connected to the chip through a vibration transfer part to mix the sample and the magnetic beads in the chip, the vibration transfer part attached to the chip to transfer vibration to the chip; a laser generator attached to the chip to supply a laser; and an anti-evaporation part attached to the chip to prevent the sample from evaporating.

The present invention also provides a cell lysis chip for the apparatus for the disruption of cells or viruses, including: a chip body having opened top surface and bottom surface and including a reaction chamber, an inlet hole, and an outlet hole; a chip cover which is attached to the top surface of the chip body to close the upper portion of the reaction chamber, allows a laser to pass through, and has an inlet hole and an outlet hole; and a chip bottom attached to the bottom surface of the chip body through a chip bonding part to close the lower portion of the reaction chamber, the inlet hole, and the outlet hole.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1:
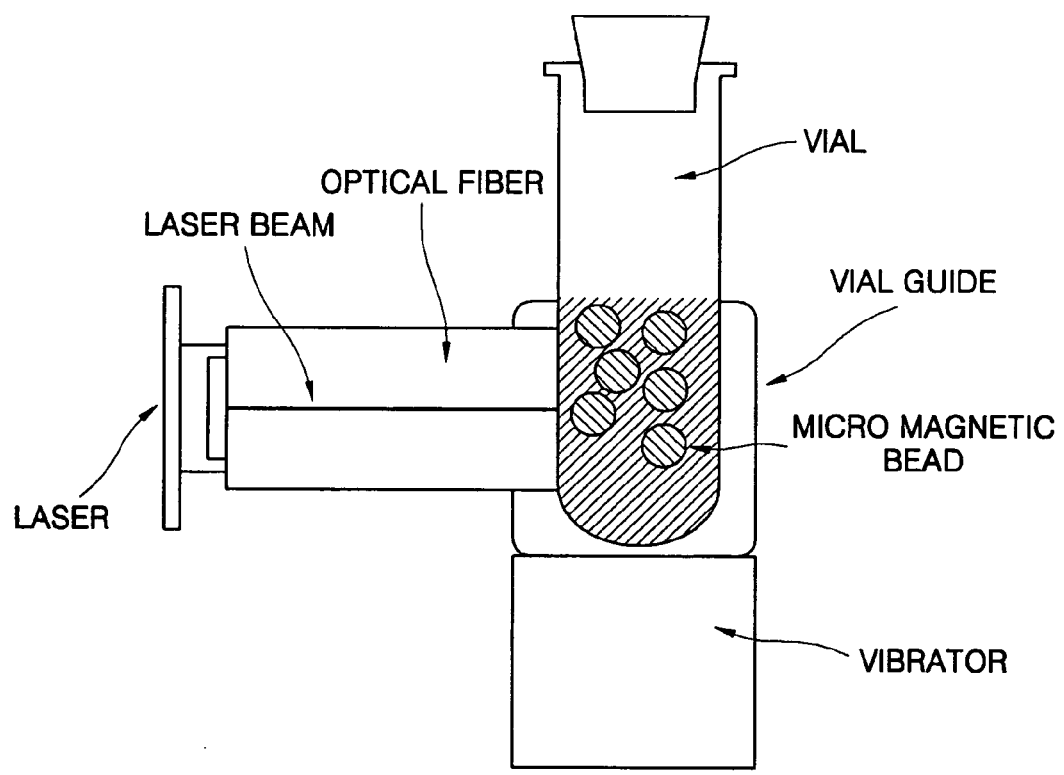
FIG. 1 is a schematic diagram of a system used for cell lysis using micro magnetic beads and a laser.

Hereinafter, the present invention will be described in more detail.

A method of disrupting cells or viruses according to an embodiment of the present invention includes: adding magnetic beads to a solution containing cells or viruses; vibrating the magnetic beads; and irradiating a laser to the magnetic beads to disrupt the cells or viruses.

In this method, a laser is irradiated onto a solution containing magnetic beads and the magnetic beads cause an ablation due to the energy of the laser to transfer shock waves, vapor pressure and heat to the cell surface. At this time, physical shocks are also applied to the cell surface. The magnetic beads heated by the laser raise the temperature of the solution and directly disrupt the cells. The magnetic beads in the solution do not act as a simple heat conductor but apply thermal, mechanical and physical shocks to the cell surface, thereby efficiently disrupting the cell surface.

The rapid cell lysis using magnetic beads and a laser is performed by heating and laser ablation in a liquid medium. The laser in combination with the micro magnetic beads converts the heat source into physical and mechanical shocks of highly heated magnetic beads to improve cell lysis. Recently, small size, high power laser diodes are rapidly being developed and a very small cell lysis apparatus using the same will be capable of being installed on a Lap-on-a-Chip (LOC). Moreover, the laser can concentrate the power and energy on a specific region on a chip by means of an optical fiber, mirror or lens or directly do so.

The best advantage of the magnetic beads is to reduce DNA isolation steps because the cell lysis by means of the micro magnetic beads and laser results in the denaturation of proteins. The denatured proteins and cell debris are attached to the magnetic beads to be removed by gravity or magnetic force. As a result, a detection limit is lowered, a DNA extraction time is significantly shortened due to an omission of one step in the DNA extraction process, polymerase chain reaction (PCR) analysis results are significantly improved due to an increase in the signal amplitude. The total time required to disrupt a cell using the micro magnetic beads and laser is only 40 seconds.

A laser ablation refers to a phenomenon caused by materials exposed to a laser beam. The laser ablation rapidly raises the temperature of a material surface from several hundred to several thousand degrees. If the temperature of the material surface is raised to the evaporation point or higher, the saturated vapor pressure on the surface rapidly increases according to an evaporation of the liquid phase material. The saturated vapor pressure is expressed as a function of temperature by a Clausius-Clapeyron equation, and is usually raised to several ten atm or more in the case of a high power pulse laser process. A pressure applied to a material surface by vapor upon the spurt of vapor is referred to as "repulsive pressure" and the magnitude of the repulsive pressure is about 0.56 $P_{sat}$ where $P_{sat}$ denotes a vapor pressure.

A shock wave is generated in a process using a laser with very large instantaneous intensity, such as a pulse laser. The vapor generated on the surface of a material heated to the evaporation point or higher for short time ranging from several nano second to several ten nano second is increased to the pressure from several atm to several ten atm and forms shock wave while expanding into the surrounding air. Due to the very high pressure, the expanding vapor applies about 0.56 $P_s$ (where $P_s$ denotes a saturated vapor pressure in the surface) to a material.

In an embodiment of the present invention, the laser can include a pulse laser or continuous wave (CW) laser.

At too low laser power, the laser ablation cannot effectively occur. The laser power is 10 mW or more for the CW laser and 1 mJ/pulse or more for the pulse laser. Preferably, the pulse laser is 3 mJ/pulse or more and the CW laser has the power of 100 mW or more. This is because when the CW is less than 10 mW and the pulse laser is less than 1 mJ/pulse, sufficient energy to disrupt the cells is not transferred.

In an embodiment of the present invention, the laser should be generated in a specific wavelength range where magnetic beads absorb the energy of the laser. The laser is generated preferably in the wavelength range of 400 nm or more, and more preferably in the wavelength range from 750 nm to 1300 nm. This is because DNA is denatured or damaged at a wavelength less than 400 nm. The laser can also be generated in one or more wavelength ranges. That is, the laser can have one wavelength or two or more different wavelengths within the above range.

In an embodiment of the present invention, the diameter of the magnetic beads is preferably from 50 nm to 1,000 μm, and more preferably from 1 μm to 50 μm. When the diameter of the magnetic beads is less than 50 nm, physical and mechanical shocks are insufficient to cause cell lysis. When the diameter of the magnetic beads is greater than 1,000 μm, it is not suitable for LOC. The magnetic beads can also be a mixture of beads with two or more sizes. That is, the magnetic beads can have equal sizes to each other or be a mixture of beads with different sizes.

In an embodiment of the present invention, the magnetic beads can be any material magnetized. In particular, the magnetic beads preferably include at least one material selected from the group consisting of ferromagnetic Fe, Ni, Cr and oxides thereof.

In an embodiment of the present invention, the magnetic beads can be polymers, organic materials, silicon or glass coated with a ferromagnetic metal.

In an embodiment of the present invention, the surface of the magnetic bead is preferably negatively charged so that DNA is not attached thereto. Since DNA is negatively charged, it is not attached to the magnetic bead, which is negatively charged, due to repulsive forces. When DNA is attached to the magnetic bead, it is difficult to isolate DNA from magnetic beads after disrupting cells, which makes DNA purification difficult.

In an embodiment of the present invention, a functional group on the surface of magnetic beads may be hydrophilic and the solution containing magnetic beads may have a pH of 6-9. The amplification efficiency of DNA obtained from lyzed cells can vary depending on the functional group on the surface of magnetic beads and the pH of the solution containing magnetic beads. As hydrophilicity of the functional group increases, the amplification efficiency of DNA after cell lysis increases. Preferably, the functional group is a carboxy group with a negative charge or a derivative thereof. The derivative of the carboxy group includes iminodiacetic acid (IDA), ethylenediaminetetraacetic acid (EDTA), citric acid, polycarboxylic acid, etc. The pH of the solution containing magnetic beads is preferably 6-9. If the pH is outside the above range, the amplification efficiency of DNA after cell lysis decreases.

In an embodiment of the present invention, the solution can be selected from the group consisting of saliva, urine, blood, serum and cell culture solutions. The solution can be any solution having nucleic acids, such as animal cells, plant cells, bacteria, viruses, phage and the like.

An apparatus for the rapid disruption of cells or viruses according to another embodiment of the present invention includes: a cell lysis chamber having an inlet hole through which a sample and micro magnetic beads are introduced; a vibrator attached to the chamber and mixing the sample and micro magnetic beads in the chamber; and a laser generator attached to the chamber and supplying a laser.

FIG. 1 is a schematic diagram of an embodiment of a system used for cell lysis using a laser and macro magnetic beads. Samples are supplied through an inlet hole. The samples are thoroughly mixed with magnetic beads. The thorough mixing of the samples and the magnetic beads is achieved by a vibrator. A laser is irradiated while vibrating the mixture. A cell lysis chamber window should be composed of a material through which the laser can sufficiently pass. The magnetic beads exposed to the laser transform light to heat, i.e. occur laser ablation. Heat, vibration, shock wave, vapor pressure, etc. are efficiently transferred due to effective heat transfer and collision of the magnetic beads with cells by continuous vibration. While the temperature of the cell lysis chamber is raised by the laser, a paraffin valve is opened, which can be controlled by the thickness of the paraffin valve. After enough cells are disrupted, the laser is turn off and remaining micro magnetic beads are removed with an electromagnet. If the paraffin valve is removed by heat, the resulting solution runs to a PCR chamber where the purified DNA is amplified.

In an embodiment of the present invention, the vibrator can include sonicators, vibrators using a magnetic field, vibrators using an electric field, mechanical vibrators such as a vortex etc., or piezoelectric materials. The vibrator is attached to the cell lysis chamber and can be any device capable of vibrating the mixed solution of the cells and the micro magnetic beads.

In an embodiment of the present invention, the apparatus for the rapid disruption of cells or viruses can further include an electromagnet attached to the cell lysis chamber and removing the magnetic beads in the cell lysis chamber after cell lysis is completed. The electromagnet can be attached to the cell lysis chamber, and for the purpose of the LOC implementation, the magnetic beads are removed by the electromagnet after cell lysis is completed so that the disrupted cell solution can directly run to a PCR chamber without performing separation of the magnetic beads. The beads should be magnetized in order to be removed by the electromagnet.

In an embodiment of the present invention, if more completely purified DNA is desired, the apparatus for the rapid disruption of cells or viruses can further include a DNA purification chamber connected to the cell lysis chamber through a channel before a PCR chamber. The DNA purification chamber is attached to the cell lysis chamber in order to purify the DNA if the paraffin valve or a valve of a MEMS structure using magnetic field or electric field is opened after cell lysis is completed.

In an embodiment of the present invention, the apparatus for the rapid disruption of cells or viruses can further include a paraffin valve located in a channel connected to the cell lysis chamber, the thickness of which is controlled by the cell lysis time. While the temperature of the cell lysis chamber is raised by the laser, the paraffin valve is opened, which can be controlled by the thickness of the paraffin valve.

In an embodiment of the present invention, the apparatus for the rapid disruption of cells or viruses can further include a DNA amplification chamber connected to the cell lysis chamber through a channel. Since the effects of purification by the micro magnetic beads are generated as described above, the DNA amplification chamber can be directly attached to the cell lysis chamber.

In an embodiment of the present invention, the apparatus for the rapid disruption of cells or viruses can further include a DNA amplification chamber connected to the DNA purification chamber through a channel. For the purpose of the LOC implementation, an amplification system of the purified DNA is necessary. The purified DNA can be detected using a spectrophotometer, micro magnetic beads, an electrochemical method, electrochemiluminescence, radiation and fluorescent label, a real-time PCR method, and the like. The PCR method is most suitable to sufficiently amplify a desired DNA. Other DNA amplification methods can be applied and direct detection through the real-time PCR method, etc. is also possible.

An apparatus for the disruption of cells or viruses according to another embodiment of the present invention includes: a cell lysis chip having an inlet hole through which a sample and magnetic beads are introduced; a vibrator connected to the chip through a vibration transfer part to mix the sample and the magnetic beads in the chip, the vibration transfer part attached to the chip to transfer vibration to the chip; a laser generator attached to the chip to supply a laser; and an anti-evaporation part attached to the chip to prevent the sample from evaporating.

Figure 2A:
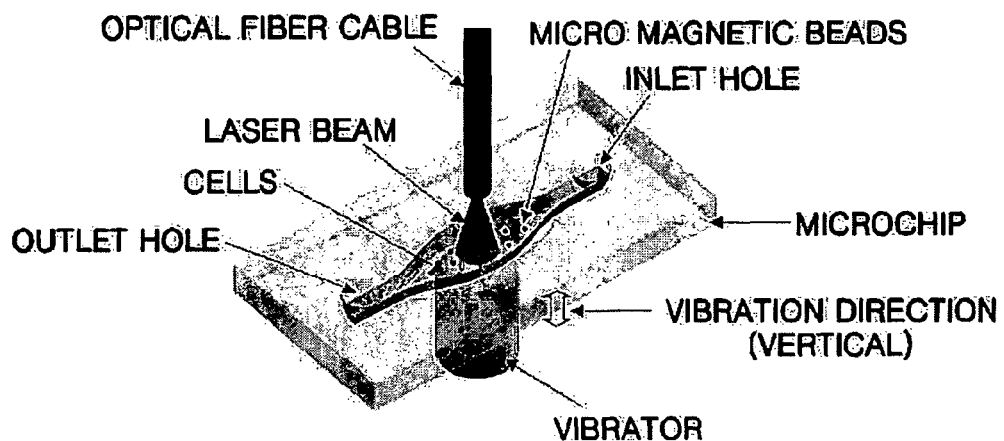
FIG. 2A is a schematic diagram of a system used in cell lysis on a microchip using a laser and micro magnetic beads according to an embodiment of the present invention.
Figure 2B:
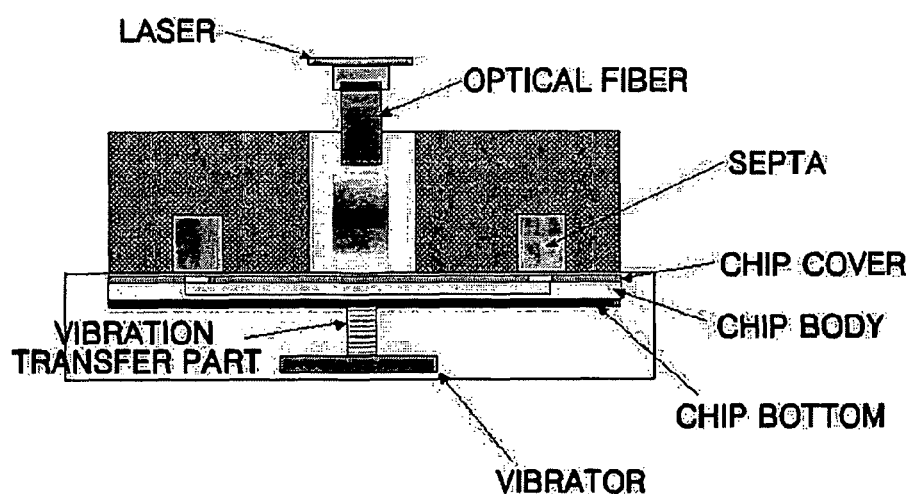
FIG. 2B is a design of the system illustrated in FIG. 2A.

FIG. 2A is a schematic diagram of an embodiment of a system used in cell lysis using a laser and micro magnetic beads on a microchip and FIG. 2B is a design of the system illustrated in FIG. 2A. A cell lysis chip is a device for lyzing cells or viruses using a sample and magnetic beads introduced through an inlet hole. The cell lysis chip includes a chip cover, a chip body, a chip bonding part, and a chip bottom. The elements of the cell lysis chip will be described in more detail later. The cell lysis chip functions as a reaction chamber in which cells or viruses are lyzed.

The vibrator is connected to the cell lysis chip through a vibration transfer part and mixes a sample and magnetic beads in the cell lysis chip. The vibrator may vertically vibrate. The vibrator can include sonicators, vibrators using a magnetic field, vibrators using an electric field, mechanical vibrators such as a vortex etc., or piezoelectric materials. The vibrator can be any device capable of vibrating the mixed solution of cells and micro magnetic beads. The vibrator may be a vibration motor for mobile phones.

The vibration transfer part transfers vibration generated by the vibrator to the chamber through the bottom surface of the cell lysis chip. The vibration transfer part may be composed of a metal such as aluminum.

The laser generator is attached to the cell lysis chip and supplies a laser to the cell lysis chip.

Figure 3:
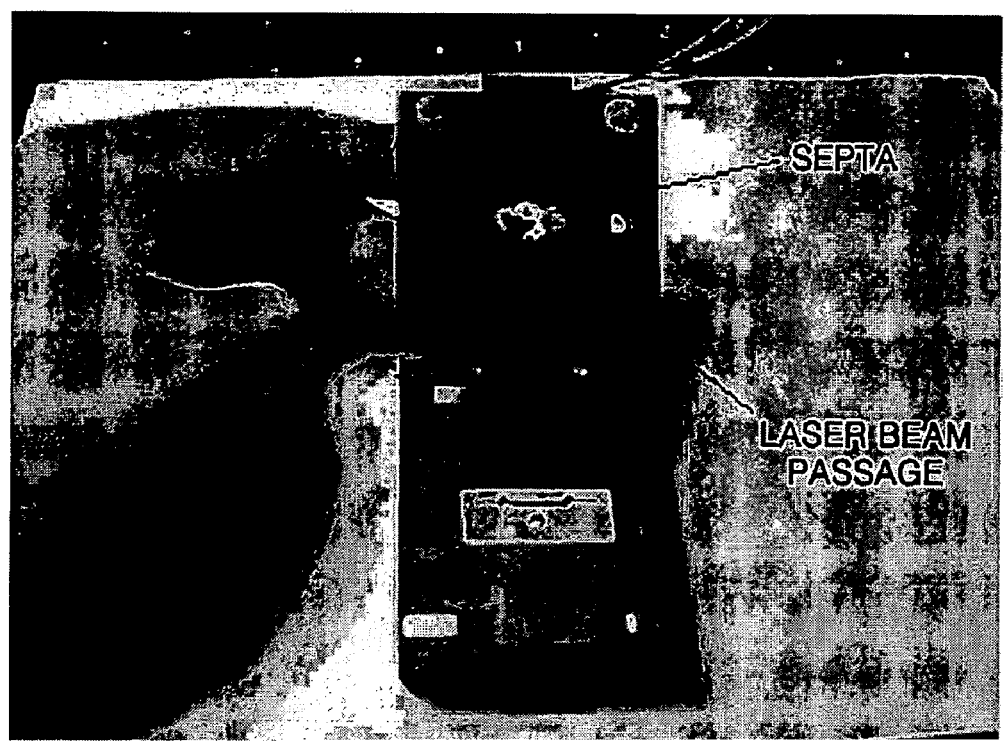
FIG. 3 is a photograph of a septa part of a cell lysis apparatus.

The anti-evaporation part is attached to the cell lysis chip to prevent the sample from evaporating. When cells are lyzed using a laser, evaporation occurs due to increase in temperature. Thus, the anti-evaporation part is necessary to reduce the evaporation. The anti-evaporation part should have a structure capable of withstanding a pressure of 10 psi or more. The anti-evaporation part can comprise septa. It is possible that an optic tape is attached to the inlet hole and the outlet hole, and then septa are fixed to the cell lysis chip. FIG. 3 is a photograph of septa of the cell lysis apparatus. The septa may be valves, polymer structures or metal structures, but they are not particularly restricted to these as long as they can prevent evaporation.

In an embodiment of the present invention, the laser can include a pulse laser or continuous wave (CW) laser.

At too low laser power, the laser ablation cannot effectively occur. The laser power is 10 mW or more for the CW laser and 1 mJ/pulse or more for the pulse laser. This is because when the CW is less than 10 mW and the pulse laser is less than 1 mJ/pulse, sufficient energy to disrupt the cells is not transferred.

In an embodiment of the present invention, the laser should be generated in a specific wavelength range where magnetic beads absorb the energy of the laser. The laser is generated preferably in the wavelength range of 400 nm or more, and more preferably in the wavelength range from 750 nm to 1300 nm. This is because DNA is denaturated or damaged at a wavelength less than 400 nm. The laser can also be generated in one or more wavelength ranges. That is, the laser can have one wavelength or two or more different wavelengths within the above range.

In an embodiment of the present invention, the diameter of the magnetic beads is preferably from 50 nm to 1,000 μm, and more preferably from 1 μm to 50 μm. When the diameter of the magnetic beads is less than 50 nm, physical and mechanical shocks are insufficient to cause cell lysis. When the diameter of the magnetic beads is greater than 1,000 μm, it is not suitable for LOC. The magnetic beads can also be a mixture of beads with two or more sizes. That is, the magnetic beads can have equal sizes to each other or be a mixture of beads with different sizes.

In an embodiment of the present invention, the magnetic beads can be any material magnetized. In particular, the magnetic beads preferably include at least one material selected from the group consisting of ferromagnetic Fe, Ni, Cr and oxides thereof.

In an embodiment of the present invention, the magnetic beads can be polymers, organic materials, silicon or glass coated with a ferromagnetic metal.

In an embodiment of the present invention, the surface of the magnetic bead is preferably negatively charged so that DNA is not attached thereto. Since DNA is negatively charged, it is not attached to the magnetic bead, which is negatively charged, due to repulsive forces. When DNA is attached to the magnetic bead, it is difficult to isolate DNA from magnetic beads after disrupting cells, which makes DNA purification difficult.

In an embodiment of the present invention, the sample can be selected from the group consisting of saliva, urine, blood, serum and cell culture solutions. The sample can be any material having nucleic acids, such as animal cells, plant cells, bacteria, viruses, phage and the like.

A cell lysis chip for the apparatus for the disruption of cells or viruses according to another embodiment of the present invention includes: a chip body having opened top surface and bottom surface and including a reaction chamber, an inlet hole, and an outlet hole; a chip cover which is attached to the top surface of the chip body to close the upper portion of the reaction chamber, allows a laser to pass through, and has an inlet hole and an outlet hole; and a chip bottom of the chip body attached to the bottom surface through a chip bonding part to close the lower portion of the reaction chamber, the inlet hole and the outlet hole.

Figure 4:
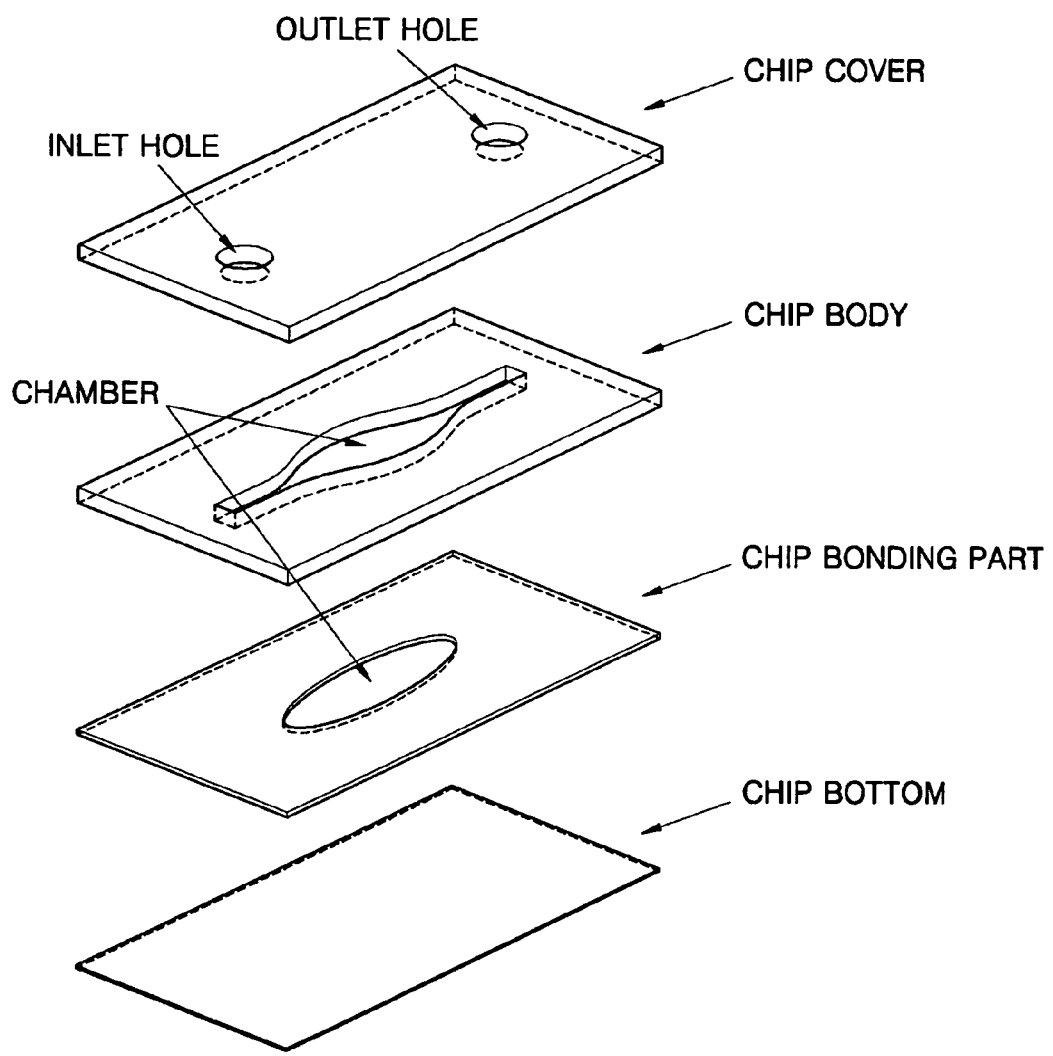
FIG. 4 is a schematic diagram of an embodiment of a microchip used in an apparatus for disrupting cells using micro magnetic beads and a laser.

FIG. 4 is a schematic diagram of an embodiment of a microchip used in an apparatus for disrupting cells using micro magnetic beads and a laser. Referring to FIG. 4, a chip body has opened top surface and bottom surface and includes a reaction chamber, an inlet hole, and an outlet hole. The chip body may be a silicon wafer which can withstand a temperature of 100° C. or higher. The chip body may be composed of glass, polymer or silicone. Glass is preferably Pyrex 7740. The chip body has a top surface to which a chip cover is attached and a bottom surface to which a chip bonding part is attached. The inner surface of the chip body may be hydrophobically treated in order to prevent bubbles from generating. For example, the inner surface of the chip body may be coated with Sigmacoat.

A chip cover is attached to the top surface of the chip body to close the upper portion of the reaction chamber. The chip cover allows a laser to pass through and has an inlet hole and an outlet hole. The chip cover may be composed of glass, polymer, indium tin oxide (ITO) glass, etc. Glass is preferably Pyrex 7740. Preferably, the material for the chip cover withstands a high temperature and has a transmittance of 90% or more. The chip cover can have an anti-reflection (AR) coating to increase the transmittance of a laser. The anti-reflection coating can be formed using a method known in the art. Thus, the chip cover can be prepared using an AR coated Pyrex 7740.

A chip bottom is attached to the bottom surface of the chip body through a chip bonding part to close the lower portion of the reaction chamber, the inlet hole and the outlet hole. The chip bottom may be composed of polymer, silicone, glass, ITO glass, etc. Preferably, the material for the chip bottom withstands a high temperature and is flexible. The chip bottom is preferably composed of a material capable of effectively transferring vibration generated by a vibrator to the chip body, for example, a polycarbonate film.

Figure 5:
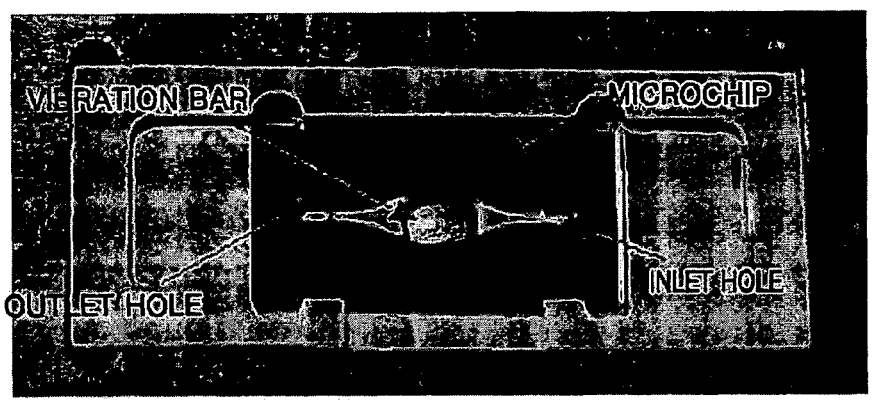
FIG. 5 is a photograph of a microchip according to an embodiment of the present invention.

The chip bonding part attaches the chip bottom to the chip body and acts as an aid of the reaction chamber containing a sample. The attachment is achieved by means of an adhesive material selected from the group consisting of an adhesive tape and an adhesive. Although the reaction chamber can be formed using only the chip body and the chip bottom, leakage of a reaction solution may take place. The chip bonding part can prevents the leakage of a reaction solution. FIG. 5 is a photograph of a microchip according to an embodiment of the present invention.

The present invention will now be described in greater detail with reference to the following examples. The following examples are for illustrative purposes only and are not intended to limit the scope of the invention.

PREPARATION EXAMPLE 1

Cell Lysis System

As illustrated in FIG. 1, bacterial cells prepared as describe below (90 μl) and micro magnetic beads (30 μl, Dynabeads® M-270 Carboxylic Acid, DYNAL, Norway) were mixed in a vial located in a vial guide (AMITECH, Korea). 808 nm, 13.8 W high power laser beam (HLU25F100-808, LIMO, Germany) was applied to the mixture for disrupting cells for a specific time in individual experiments while stirring the vial by vortexing (see FIG. 1).

PREPARATION EXAMPLE 2

Bacterial Strain and the Determination of Bacterial Cell Viability

*E. coli* strain BL21 and *Streptococcus mutans* (ATCC# 35668) were cultured at 37° C. with vigorous aeration in brain heart infusion (BHI) media to exponential phase ($OD_{600}$=0.5~1.0). The bacterial cells were harvested by centrifugation and washed twice with 3 ml of phosphate-buffered saline (PBS) solution. The cells were resuspended in PBS (cell density; $1\times10^5$ cells/μl). The number of viable cells was determined by the ability of single cells to form colonies. Aliquots of *E. coli* cells ($1\times10^3$) after laser beam radiation were spread onto BHI plates. The plates were incubated at 37° C. overnight, and the number of colonies was counted.

A *Staphylococcus epidermidis* (ATCC#14990→12228) was cultured at 37° C. with vigorous aeration in Nutrient Agar (NA) media to exponential phase ($OD_{600}$=0.5~1.0). The bacterial cells were harvested by centrifugation and washed twice with 3 ml of phosphate-buffered saline (PBS) solution. The cells were resuspended in PBS (cell density; $1\times10^5$ cells /μl). The number of viable cells was determined by the ability of single cells to form colonies. Aliquots of *Staphylococcus epidermidis* cells ($1\times10^3$) after laser beam radiation were spread onto NA plates. The plates were incubated at 37° C. overnight, and the number of colonies was counted.

PREPARATION EXAMPLE 3

Extraction of Bacterial Genomic DNA

In order to compare the efficiency of DNA release by laser method with the efficiency of other known conventional methods, *E. coli* genomic DNA (from $0.9\times10^5$ cells equivalent to the number of cells used for each laser lysis) was prepared using the boiling method for 5 min at 95° C.

PREPARATION EXAMPLE 4

Quantitation of DNA Release from Bacteria

To monitor cell lysis and to quantitate the amount of DNA released from lyzed cells, Agilent Bioanalyzer followed by polymerase chain reaction (PCR) amplification was used. The following pair of primers were used for PCR: primer A (SEQ ID No: 1); primer B (SEQ ID No: 2). This pair of primer is complementary to each end of a gene encoding the 16S ribosomal RNA, allowing the amplification of its entire coding region during PCR.

*E. coli* PCR amplification was carried out using Taq polymerase (Solgent. Co, Ltd, Korea) for 25 cycles (95° C. for 1 min to pre-denature, 95° C. for 5 s to denature, 60° C. for 13 s to anneal, and 72° C. for 15 s to extend, and 72° C. for 1 min to additionally extend). For Gram-positive bacterial cells; *Streptococcus mutans* and *Staphylococcus epidermidis* PCR amplification were carried out using Taq polymerase (Solgent. Co, Ltd, Korea) for 30 cycles (95° C. for 1 min to pre-denature, 95° C. for 5 s to denature, 60° C. for 13 s to anneal, and 72° C. for 15 s to extend, and 72° C. for 1 min to additionally extend). After amplification cycles are completed, a melting curve was acquired by slowly heating (0.1° C./s) the sample from 60 to 90° C. The PCR was performed by LightCycler® (Roche Diagnostics Corporation, IN, USA) with a total volume of 20 μl reaction mixture containing 1× FastStart DNA Master SYBR (Roche Diagnostics Corporation, IN, USA), 0.25 μM of forward and reverse primers (Genotech, Korea), 4 mM $MgCl_2$ (Roche Diagnostics Corporation), D.W (PCR grade, Roche Diagnostics Corporation, IN, USA). The amplified DNAs were analyzed in an Agilent BioAnalyzer 2100 (Agilent Technologies, Palo Alto, Calif.) using commercially available DNA 500 assay sizing reagent sets.

PREPARATION EXAMPLE 5

Fabrication of Cell Lysis Chip of the Present Invention

Microchips with a chip size of 7.5 mm×15 mm for 10 µl sample volume were fabricated using silicone, glass, polycarbonate film, and Double Coated Tape (9495MP, 3M, MN, USA). As shown in FIG. 4, for laser-induced sample preparation, the fabrication process consisted of two photolithography steps and a bonding step by double-coated tapes with polycarbonate film. The glass wafer with six inches diameter and a thickness of 500 µm was cleaned and laminated by a BF410 film photoresist. The photoresist was patterned by pholithography to form holes with a diameter of 1.5 mm for inlet and outlet sample passages. Holes were formed on the glass wafer by sand blast technique. The silicon wafer was a double-sided polished silicon substrate with a diameter of six inches and a thickness of 680 µm. Chamber was formed on the silicon wafer by sand blast technique due to the cost concerns. For optimization of sample loading, Sigmacoat® (Sigma-aldrich, MO, USA) was coated on the sand blasted surface of silicon wafer. And then, polycarbonate film with a thickness of 100 µm was bonded to silicon wafer using Double Coated Tape with a thickness of 150 µm.

PREPARATION EXAMPLE 6

Laser Induced On-chip Sample Preparation System

As shown in FIG. 2A, for bacterial cell lysis, bacterial cells (1 µl) prepared as below and micro magnetic beads (9 µl, approximately $9×10^6$ beads/µl, Dynabeads® MyOne™ Carboxylic Acid, DYNAL, Norway) were mixed in a microchip (SAIT, Korea) placed in a chip guide module (AMITECH, Korea). For effect of surface charge of magnetic beads and material of beads, silica beads (3.0 µm, Bangs Laboratories Inc., IN, USA), amine-terminated polystyrene magnetic beads (1.5 µm, Bangs Laboratories Inc., IN, USA), polystyrene beads (4.16 µm, Bangs Laboratories Inc., IN, USA) and carboxylic acid-terminated polystyrene magnetic beads were prepared additionally.

High power laser beam at 808 nm (1 W) was applied to disrupt cells for indicated periods using fiber-coupled laser systems (HLU25F100-808, LIMO, Germany) with 0.22 NA divergence in each experiment while the microchip was vibrated by coin-type vibration motor (DMJBRK20X, Samsung electro-mechanics, Korea) using aluminum vibration bar. The laser power was measured by 30 W Broadband Power/Energy Meter (MELLES GRIOT, US). Laser wavelength was selected by absorption coefficient of wavelength in water. Most laser beam of 808 nm with absorption coefficient of 0.021773 ($cm^{-1}$) in water is transmitted through the water and reaches the micro magnetic beads. For the purpose of the present invention, a visible laser beam is also applicable, but a high power laser diode has not been developed as a portable device and is not cost effective. In addition, the absorption coefficient of IR wavelength in water is very high; most of IR laser energy will be absorbed in water making it unsuitable for this usage. UV laser beam is not good for cell lysis and DNA purification, because it is known that UV irradiation causes DNA damage. DNA irradiated with UV accumulates a thymine dimmer as the major photoproduct. Thus, a continuous laser diode with 808 nm spectrum was used.

A vibration system for on-chip sample preparation test module using vibration motor that mostly used in mobile phone (DMJBRK20X, Samsung electro-mechanics, Korea) with aluminum (AMITECH, Korea) was designed to vibrate flexible polycarbonate film of microchip only sample chamber zone with a 12,000 rpm. Vibration power of vibration motor was adjusted by power supply (E3620A, Agilent, CA, USA). Temperature of sample in a chamber of microchip was measured by thermocouple (K type, Omega) with data acquisition system (34970A, Agilent, CA, USA). As shown in FIG. 3, both inlet and outlet holes were sealed with optically transparent adhesive tapes (Applied Biosystems, CA, USA) after loading sample solution with magnetic beads. To confirm that there is no leaking occurring during laser irradiation, both inlet and outlet holes were compressed with two elastomers (thermogreen LB-2, Sigma-Aldrich, MO, USA) located on the top cover of the on-chip sample preparation test module.

PREPARATION EXAMPLE 7

Photographs of Live and Dead Cells with Magnetic Beads

In order to observe live and dead cells remaining in the sample solution following laser irradiation was stained using the Live/Dead® BacLight™ Bacterial Viability kit (L7012, Molecular Probe, OR, USA) according to the procedure recommended by the suppliers. Images were taken by microscopy (Eclipse TE 300, Nikon, Japan).

PREPARATION EXAMPLE 8

DNA Analysis After Laser Irradiation

Genomic and plasmid DNAs were isolated from the same numbers of BL21 cells containing pCR®II-TOPO® (Invitrogen) plasmids using various methods. For the laser lysis, cells were mixed with magnetic beads and irradiated with laser for 40 sec and DNA was purified by ethanol precipitation with 0.3 M sodium acetate after Phenol/Chloroform/lsoamylalcohol cleaning. For the boiling lysis, cells were heated at 95° C. for 5 min and DNA was purified as laser lysis. Qiagen QIAprep® Miniprep kit was used to isolate the plasmids. Qiagen QIAamp® DNA Mini kit was used to isolate the genomic DNA of BL21. DNAs were run with 0.7% agarose gel with 1 kb marker.

EXAMPLE 1

Effects of Laser Irradiation on Cell Survival in the Presence of Magnetic Beads

Figure 6:
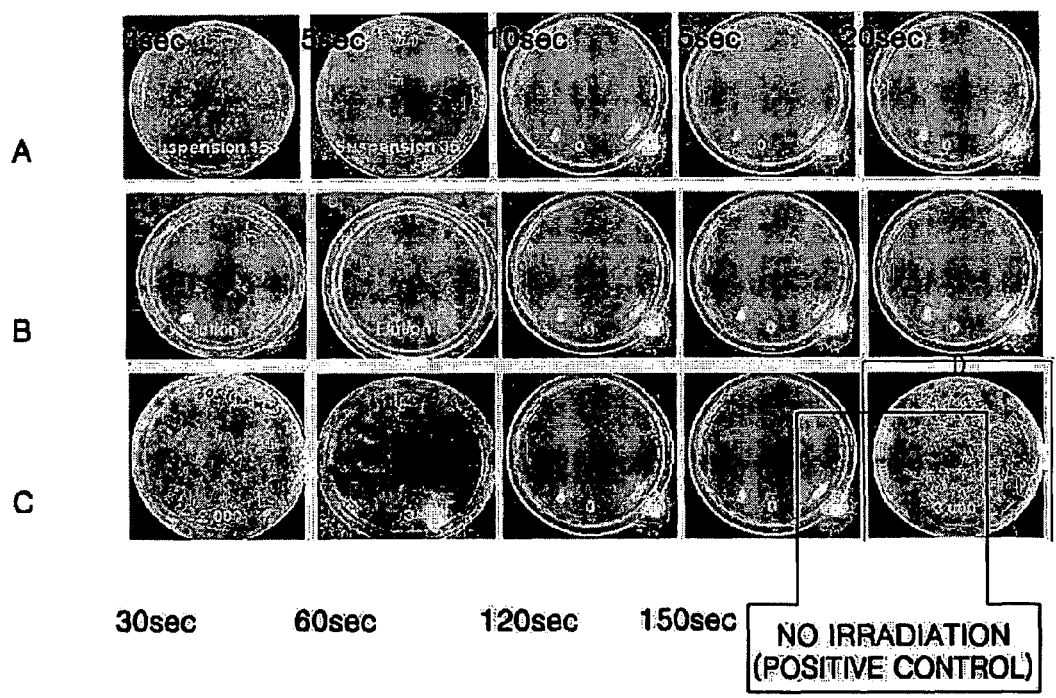
FIG. 6 illustrates the results of determining cell viability after laser irradiation.

The effects of laser irradiation on cell survival in the presence of magnetic beads were investigated. FIG. 6 illustrates the results of determining cell viability after laser irradiation. Cells ($3×10^3$) were irradiated with a laser in the presence (A and B) or absence (C) of micro magnetic beads for designated times and then spread on LB plates. The plates were incubated overnight at 37° C., and then the number of formed colonies was scored (A: cells in a suspension after laser irradiation in the presence of micro magnetic beads for designated times; B: cells recovered by washing magnetic beads after laser irradiation; C: cells under the same condition as the cells of A, except that laser irradiation was performed in the absence of micro magnetic beads; note that cells were irradiated with laser beam for prolonged periods; D: a positive control without laser irradiation).

As seen from FIG. 6, bacterial cells lost viability due to laser irradiation. The loss of viability was sharply increased by adding the magnetic beads. After laser irradiation for 3 seconds, 5% of the initial cells (153 cells among 3000 cells) were survived in the presence of the magnetic beads and after laser irradiation for 10 seconds, no cell survived (FIG. 6A). In contrast, in the absence of the magnetic beads, even after laser irradiation for 30 seconds, about two thirds of the initial cells (about 2000 cells) survived (FIG. 6C). To identify that cells nonspecifically bonded to the beads, the beads were washed with a high salt buffering solution (PBS+0.3 M NaCl) and the washing solution was also inspected for living cells (FIG. 6B). A small number of living cells were recovered and a survival kinetics was the same as that of cells recovered from the suspension, which indicated that cells from beads were similar to those trapped with solution between the beads. These results suggest that since laser irradiation can results in the rapid disruption of cells in the presence of magnetic beads, it can be used to release any type of DNA such as genomic, episomal or viral DNA present in living cells.

EXAMPLE 2

Effects of Laser Irradiation on DNA Release from Cells

Figure 7:
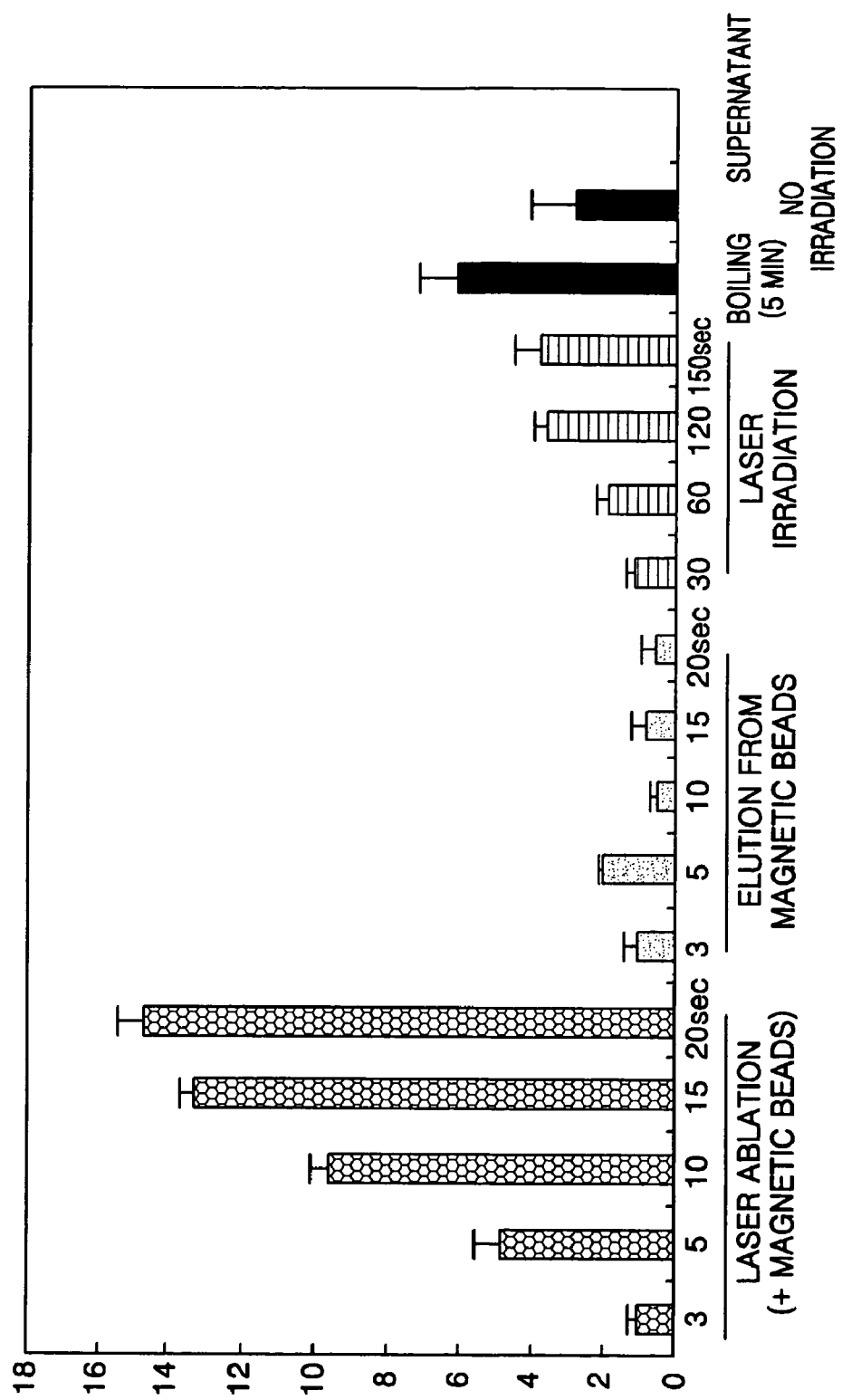
FIG. 7 shows that laser irradiation efficiently releases bacterial DNA only in the presence of magnetic beads.

Since the loss of viability as observed above was not necessarily related to cell lysis required for releasing DNA from cells, the presence of DNA in a solution was inspected by amplifying 16S rDNA using above-described PCR. FIG. 7 shows that laser irradiation efficiently releases bacterial DNA only in the presence of magnetic beads. The bars represent the concentration (ng/μl) of the amplified DNA. The amount of the PCR product was quantified by means of Agilent BioAnalyzer 2100. The error bars represent the standard deviation of the mean.

As shown in FIG. 7, 16S rDNA was most efficiently amplified when a solution was used as a template DNA source. Moreover, the amount of the PCR product was proportional to the irradiation time and the magnetic beads sharply (20 times or more) increased the PCR efficiency. These results are consistent with cell viability. That is, these results demonstrate that the loss of cell viability does not result from thermal inactivation of cells without cell lysis, but results from the physical disruption of cells.

EXAMPLE 3

Figure 8:
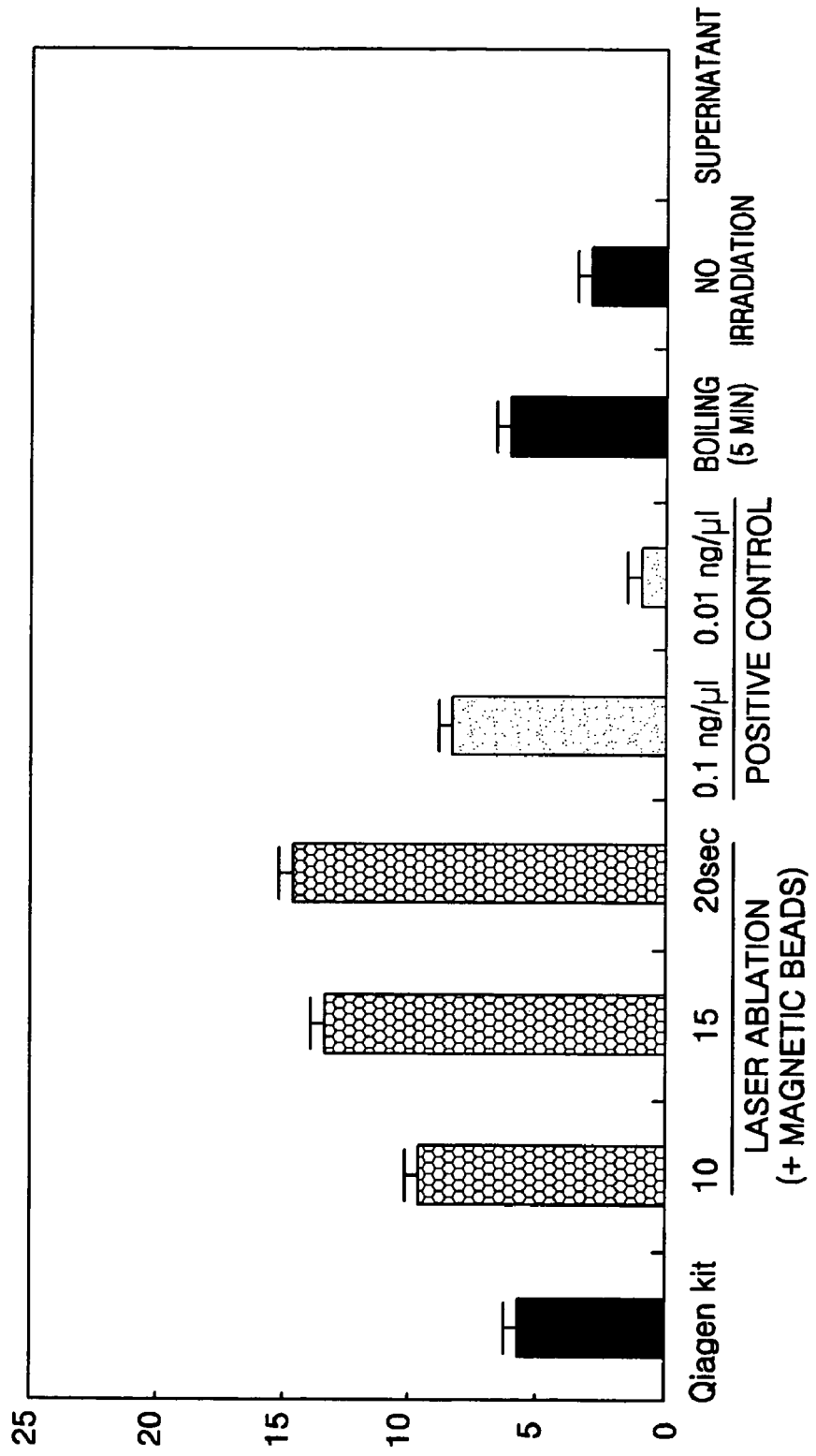
FIG. 8 shows that DNA released by laser ablation is more efficiently amplified by Taq polymerase than DNA prepared by a conventional method.

Comparison of DNA Release Efficiency of Laser Ablation Cell Lysis with Micro Magnetic Beads and Chemical Cell Lysis To directly compare a DNA release efficiency of cell lysis according to the present invention with that of a conventional chemical cell lysis, DNeasy, which was a Qiagen kit for cell lysis and the purification of released DNA, was used. FIG. 8 shows that DNA released by laser ablation is more efficiently amplified by Taq polymerase than DNA prepared by the conventional method. In all experiments, DNA was prepared by using the same number of cells. The bars represent the concentration (ng/μl) of the amplified DNA. The amount of the PCR product was quantified by means of Agilent BioAnalyzer 2100. The error bars represent the standard deviation of the mean.

As shown in FIG. 8, the 16S rDNA was more efficiently amplified with DNA obtained after laser irradiation in the presence of magnetic beads. Considering that the Qiagen kit is not optimal with samples containing small cell numbers ($<1\times10^9$), it is possible that the amounts of DNA recovered using the Qiagen kit is less than expected. Despite this, cell lysis by laser in conjunction with magnetic beads could provide a greater versatility in application due to easiness in integrating this technique to the LOC. In addition, it was observed that the efficiency of PCR amplification with DNA release by laser ablation is greater than DNA obtained with either Qiagen kit or boiling method. This indicates that laser irradiation releases DNA at least the same as or greater amounts of DNA than the other two conventional methods. If the same amounts of DNA are released, the more efficient PCR amplification with DNA from laser ablation indicates that the release of inhibiting materials is minimized by laser ablation.

EXAMPLE 4

Effects of the Size of Magnetic Beads on Cell Lysis Efficiency

Figure 9:
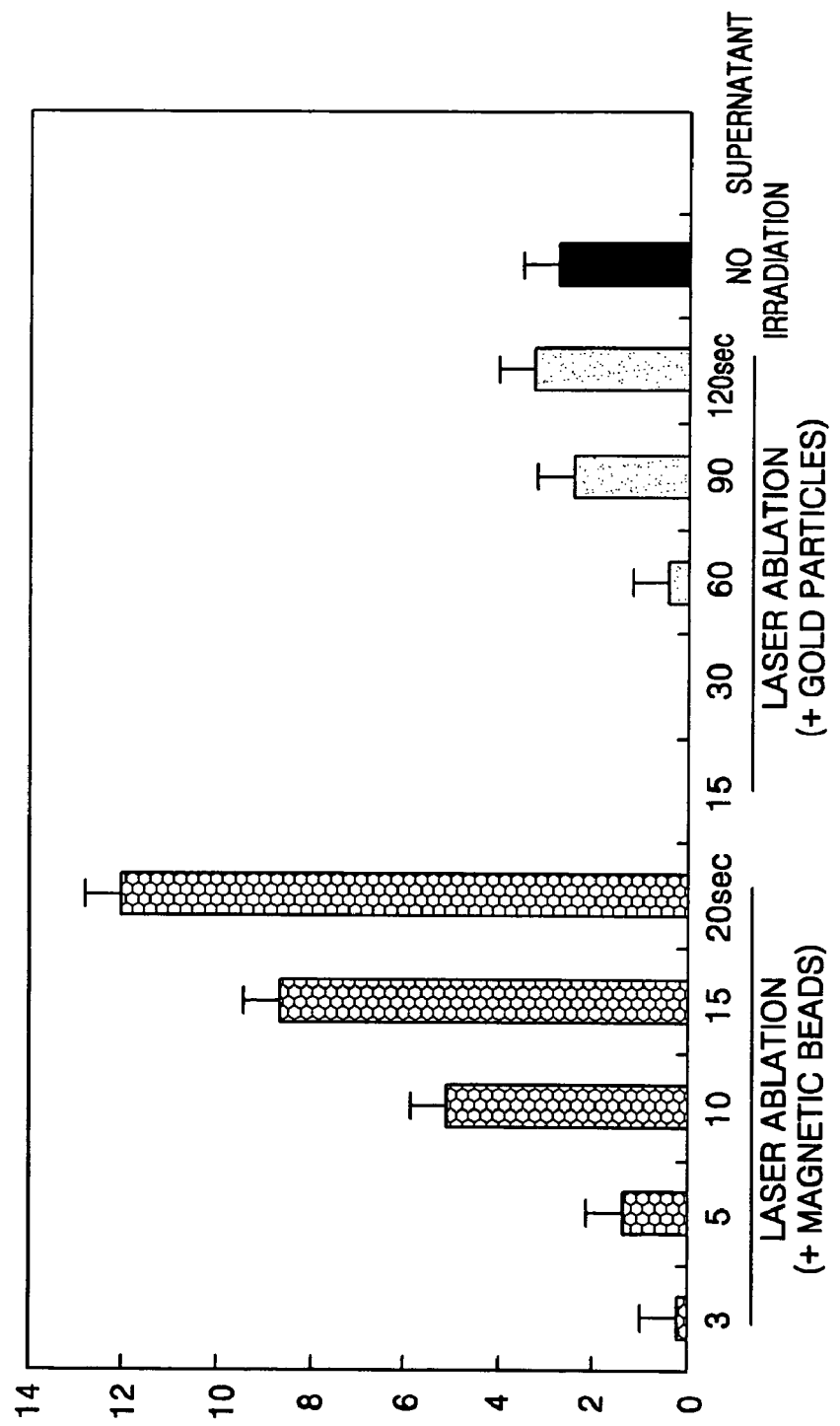
FIG. 9 shows the effects of the size of magnetic beads.

Effects of the size of magnetic beads on release of DNA from cells were investigated. FIG. 9 shows the effects of the size of the magnetic beads. The bars represent the concentration (ng/μl) of the amplified DNA. The amount of the PCR product was quantified by means of Agilent BioAnalyzer 2100. The error bars represent the standard deviation of the mean.

As shown in FIG. 9, the magnetic beads of 2.7 μm in diameter were much more efficient in cell lysis than the 5-nm gold particles (G1402, Sigma, MO, USA).

EXAMPLE 5

Laser Transmittance Test on Chip Cover

Figure 10:
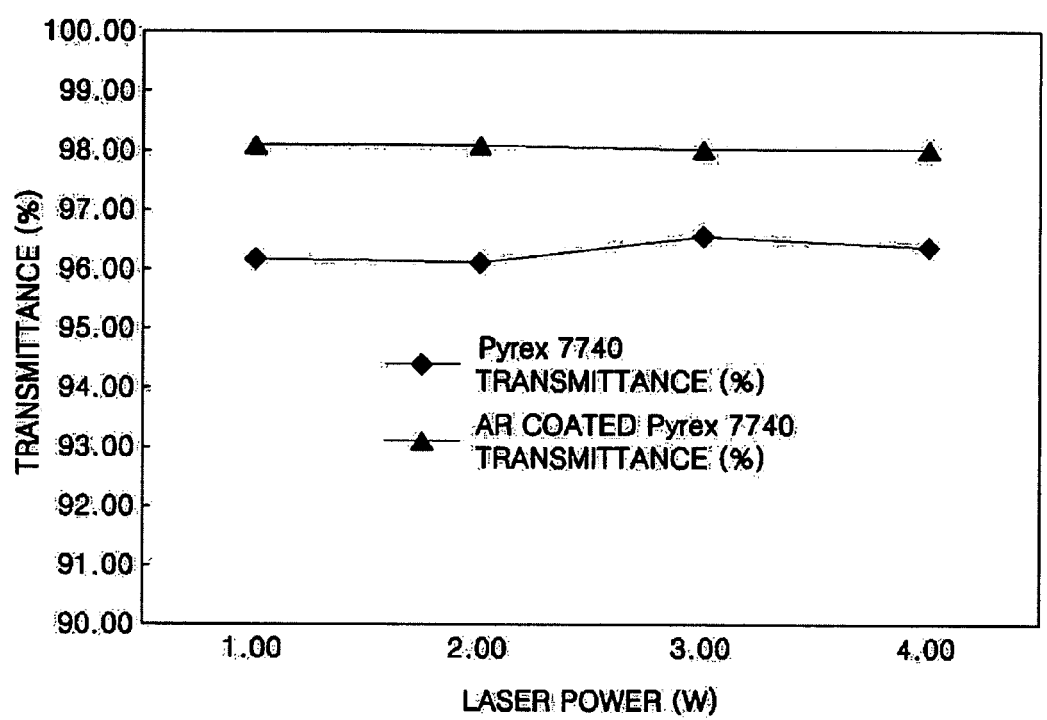
FIG. 10 is a graph illustrating the transmittance of Pyrex 7740 and anti-reflection (AR) coated Pyrex 7740.

To check that the laser generated by a laser generator can efficiently transmit a chip cover, Pyrex 7740 and AR coated Pyrex 7740 (Corning) were used as chip covers. The laser transmittance was measured using 30 W Broadband Power/Energy meter (MELLES GRIOT, US) at the laser power of 1, 2, 3, and 4 W. FIG. 10 shows laser transmittance on Pyrex 7740 and AR coated Pyrex 7740. As shown in FIG. 10, AR coated Pyrex 7740 had about 1.75% higher laser transmittance than AR uncoated Pyrex 7740. Thus, the AR coated Pyrex 7740 is suitable to efficiently provide a laser into a cell lysis chip.

EXAMPLE 6

Anti-evaporation Test on Cell Lysis Chip

Figure 11:
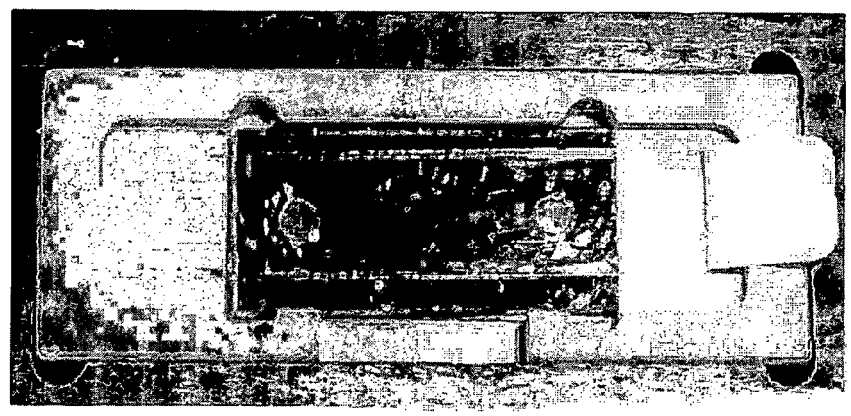
FIG. 11 is a photograph of a cell lysis chip according to an embodiment of the present invention after laser irradiation.

To check that the cell lysis chip of the present invention causes evaporation due to vapor pressure generated by a laser, an evaporation test was performed. For the cell lysis chip as prepared above, the same experiment was performed at least 200 times at the laser power of 1, 2, 3, and 4 W. FIG. 11 is a photograph of the cell lysis chip of the present invention after laser irradiation. At the laser power of 2 W or less, vapor pressure increased due to increased temperature of the sample solution, and evaporation within the cell lysis chip did not occur.

EXAMPLE 7

Effects of the Amount of Magnetic Beads on Cell Lysis Efficiency

Figure 12:
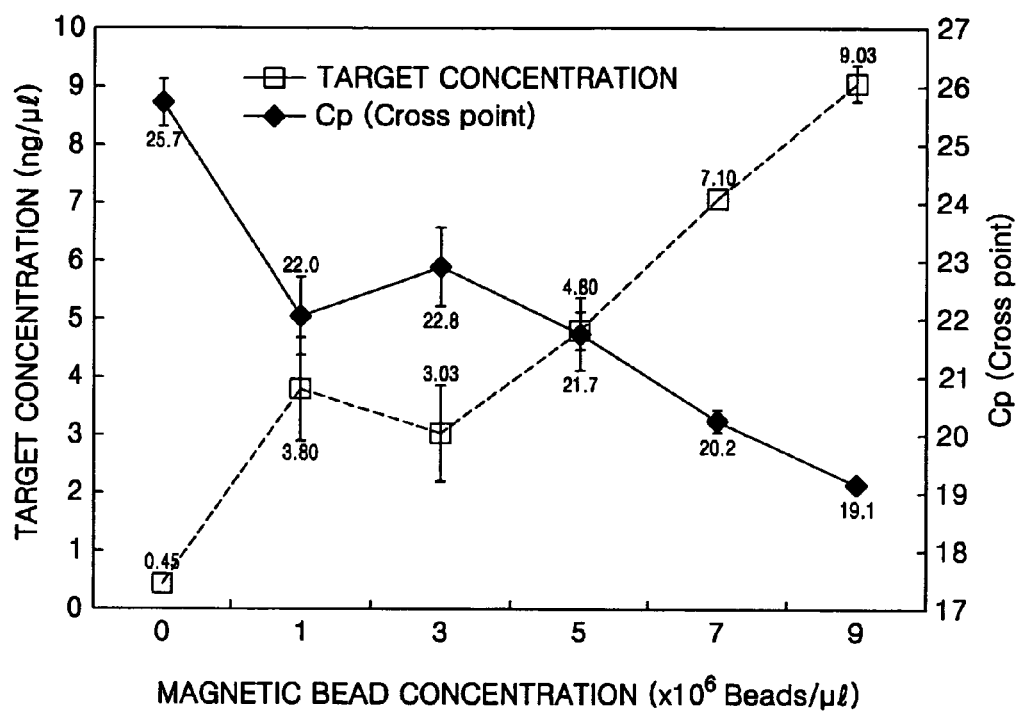
FIG. 12 is a graph illustrating PCR results of DNA released from $E.\ coli$ cells with respect to the concentration of magnetic beads.

The effects of the amount of magnetic beads on cell lysis efficiency, i.e., the amount of released DNA was investigated. Different amount of beads was added to a sample solution (0 to $9\times10^6$ beads/μl) and 1 W laser radiation power was irradiated for 40 sec at 808 nm. FIG. 12 is a graph illustrating PCR results of DNA released from *E. coli* cells with respect to the amount of magnetic beads. A crossing point (Cp) is the cycle number when detectable fluorescence is first determined in real-time PCR. That is, as the starting concentration of DNA increases, the Cp value decreases. Cp is also related to DNA purification. As the purity of DNA increases, the Cp value decreases. Thus, when the Cp value is lower, DNA in the solution is more purified form.

As shown in FIG. 12, the amount of DNA released increased as more magnetic beads were added. At the bead concentration above $5\times10^6$ beads/μl, a good efficiency for the efficient cell lysis and DNA release was yielded. Also, for accurate determination of starting target copy number, value of Cp of *E. coli* DNA amplification by LightCycler® (Roche Diagnostics Corporation, IN, USA) as known real time PCR machine was checked. As shown in FIG. 12, the value of Cp decreased as more magnetic beads were added. This result suggests that starting target copy number increased as more magnetic beads were added.

EXAMPLE 8

Effects of Vibration Power on Cell Lysis Efficiency

Figure 13:
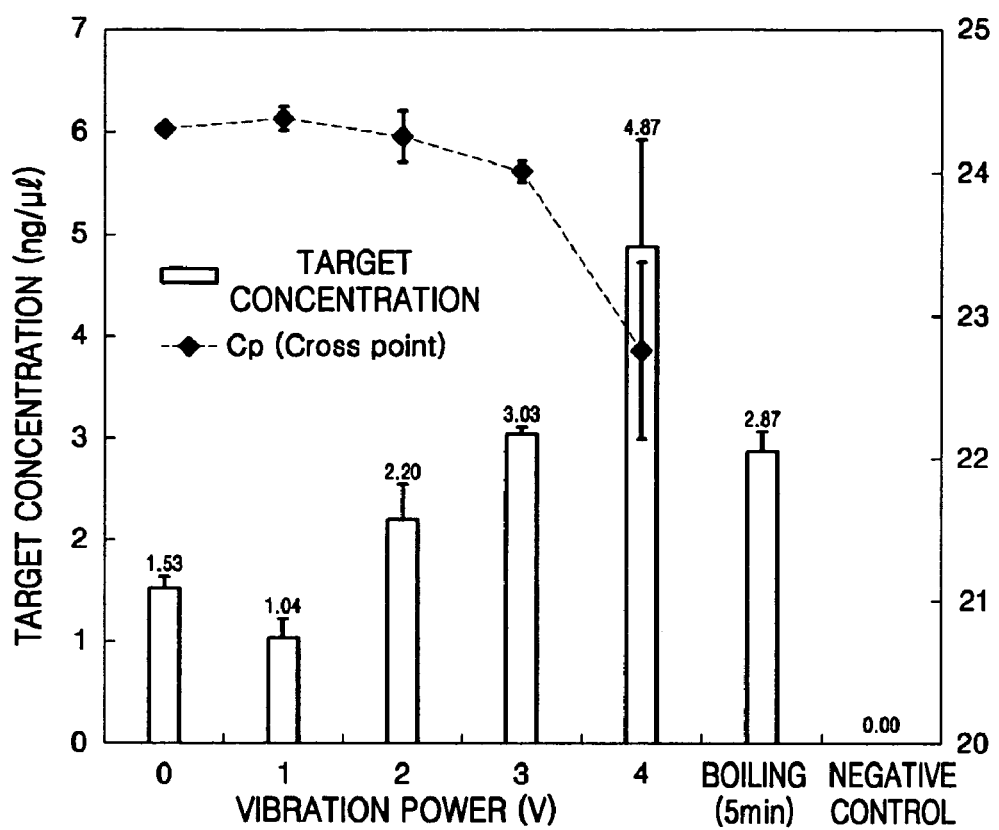
FIG. 13 is a graph illustrating PCR results of DNA released from $E.\ coli$ cells with respect to the voltage of a vibrator.

To check the effects of vibration power on cell lysis efficiency, the voltage of vibration motor of 0-4 V was used. In each reaction, *E. coli* cells ($1\times10^5$ cells/μl), which are Gram-negative bacterial cells, were used. 10 μl of a sample was irradiated with 0.5 W laser radiation power for 40 sec at 808 nm. The distance between the cell lysis chip and optical fiber was 1 mm. The concentration of beads in the sample was $5\times10^6$ beads/μl and three replicates of each condition were tested. FIG. 13 is a graph illustrating PCR results of DNA released from *E. coli* cells with respect to the voltage of vibration motor. In FIG. 13, Boiling (positive control) refers to the case when a PCR was performed on DNA released after boiling *E. coli* cells at 95° C. for 5 min; and Negative control refers to the case when a PCR was performed using only distilled water without DNA. The bars represent the concentration (ng/μl) of the amplified DNA. The amount of the PCR product was quantified by means of Agilent BioAnalyzer 2100. The error bars represent the standard deviation of the mean. As the amount of the amplified DNA increases, the number of lyzed cells increases, indicating that cell lysis efficiency increases.

As shown in FIG. 13, as the voltage of vibration motor increases, cell lysis efficiency increases. The voltage of vibration motor above 3 V was sufficient for the higher cell lysis efficiency than using boiling method. In addition, as the voltage of vibration motor increases, the amount of released DNA increases due to increased cell lysis efficiency, and thus, the Cp value decreases.

Thus, cell lysis efficiency is increased by vibration after mixing cells or viruses with magnetic beads.

EXAMPLE 9

Figure 14:
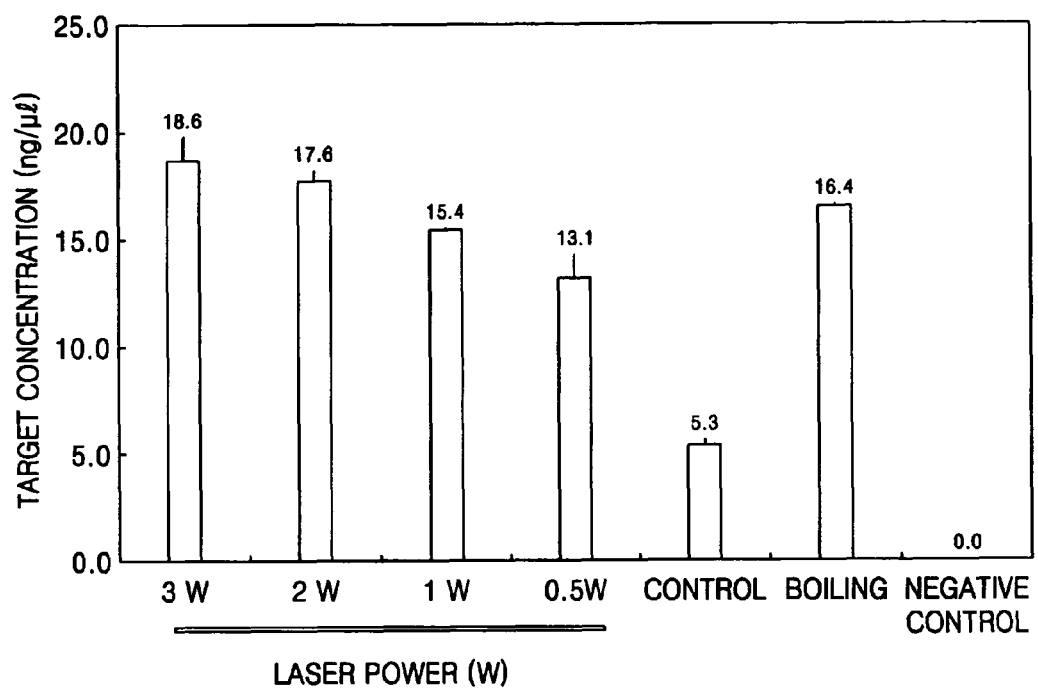
FIG. 14 is a graph illustrating PCR results of DNA released from *Staphylococcus epidermidis* cells ($1\times10^5$ cells/µl) with respect to laser power.

Effects of Laser Radiation Power on Lysis Efficiency for Gram Positive Bacterial Cells To check the effects of laser radiation power on lysis efficiency for Gram-positive bacterial cells, laser radiation power of 0.5-3 W was used. The same experiment as in Example 8 was carried out, except that *Staphylococcus epidermidis* cells ($1\times10^5$ cells/μl), which are Gram-positive bacterial cells, were used, the distance between the cell lysis chip and optical fiber was 3 mm, and the concentration of beads in the sample was $9\times10^6$ beads/μl. FIG. 14 is a graph illustrating the PCR results of DNA released from *Staphylococcus epidermidis* cells ($1\times10^5$ cells/μl). In FIG. 14, Control refers to the case when a PCR was performed on supernatant obtained after centrifuging *Staphylococcus epidermidis* cells at 13,200 rpm for 5 min; Boiling (positive control) refers to the case when a PCR was performed on DNA released after boiling *Staphylococcus epidermidis* cells at 95° C. for 5 min; and Negative control refers to the case when a PCR was performed using only distilled water without DNA. The bars represent the concentration (ng/μl) of the amplified DNA. The amount of the PCR product was quantified by means of Agilent BioAnalyzer 2100. The error bars represent the standard deviation of the mean. As shown in FIG. 14, as laser radiation power increases, cell lysis efficiency increases. Specifically, the laser radiation power above 1 W was sufficient for obtaining the same or higher cell lysis efficiency than using the boiling method. Thus, when cells or viruses are lyzed using the microchip of the present invention, laser radiation power can be significantly reduced.

To check the effects of the concentration of cells on cell lysis efficiency, the same experiment as described above was carried out, except that *Staphylococcus epidermidis* cells ($1\times10^2$ cells/μl), which are Gram-positive bacterial cells, were used.

Figure 15:
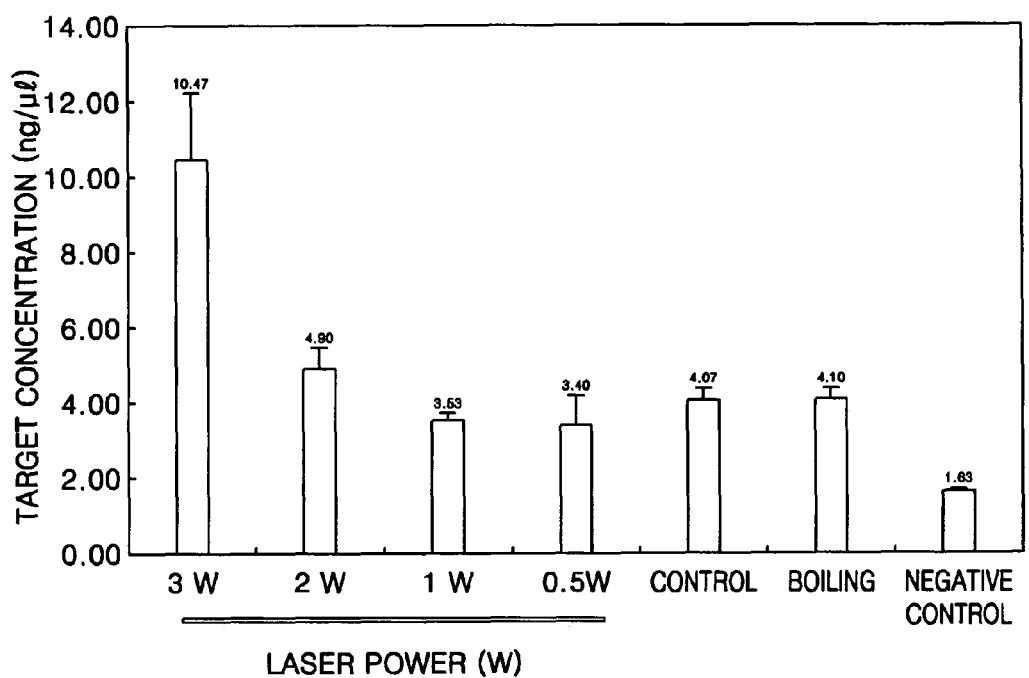
FIG. 15 is a graph illustrating PCR results of DNA released from *Staphylococcus epidermidis* cells ($1\times10^2$ cells/µl) with respect to laser power.

FIG. 15 is a graph illustrating the PCR results of DNA released from *Staphylococcus epidermidis* cells ($1\times10^2$ cells/μl) with respect to the laser power. In FIG. 15, Control refers to the case when a PCR was performed on supernatant obtained after centrifuging *Staphylococcus epidermidis* cells at 13,200 rpm for 5 min; Boiling (positive control) refers to the case when a PCR was performed on DNA released after boiling *Staphylococcus epidermidis* cells at 95° C. for 5 min; and Negative control refers to the case when a PCR was performed using only distilled water without DNA. The bars represent the concentration (ng/μl) of the amplified DNA. The amount of the PCR product was quantified by means of Agilent BioAnalyzer 2100. The error bars represent the standard deviation of the mean. As shown in FIG. 15, as laser radiation power increases, cell lysis efficiency increases. Specifically, the laser radiation power of 3 W provided much higher cell lysis efficiency than using the boiling method. Thus, regardless of the concentration of cells, Gram-positive bacterial cells can be efficiently lyzed using the method of the present invention.

In addition, to check that another Gram-positive bacterial cell *Streptococcus mutans* can be efficiently lyzed using the cell lysis chip of the present invention, the same experiment as described above was carried out, except that *Staphylococcus epidermidis* cells and *Streptococcus mutans* cells were used and laser radiation power of 1 W was used for 40 sec.

Figure 16:
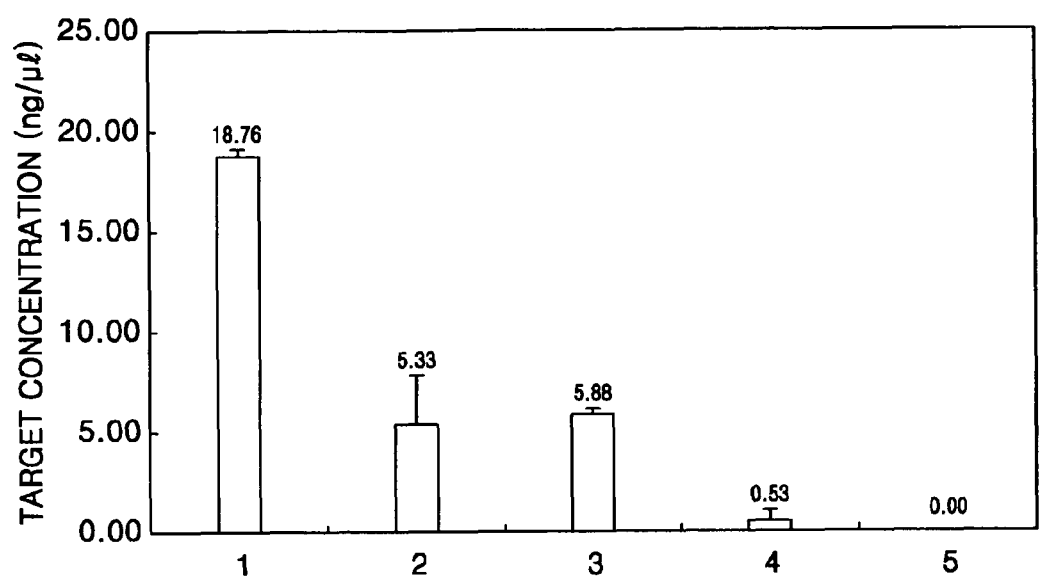
FIG. 16 is a graph illustrating PCR results of DNA released from *Staphylococcus epidermidis* cells and DNA released from *Streptococcus mutans* cells.

FIG. 16 is a graph illustrating the PCR results of DNAs released from *Staphylococcus epidermidis* cells and *Streptococcus mutans* cells. In FIG. 16, Sample 1 refers to the case when a PCR was performed on DNA released from *Staphy-* lococcus epidermidis cells; Sample 2 refers to the case when a PCR was performed on DNA released after boiling *Staphylococcus epidermidis* cells at 95° C. for 5 min; Sample 3 refers to the case when a PCR was performed on DNA released from *Streptococcus mutans* cells; Sample 4 refers to the case when a PCR was performed on DNA released after boiling *Streptococcus mutans* cells at 95° C. for 5 min; and Sample 5 refers to the case when a PCR was performed using only distilled water without DNA. The bars represent the concentration (ng/µl) of the amplified DNA. The amount of the PCR product was quantified by means of Agilent BioAnalyzer 2100. The error bars represent the standard deviation of the mean. As shown in FIG. 16, the cell lysis method of the present invention has better cell lysis efficiency on both *Staphylococcus epidermidis* cell and *Streptococcus mutans* cell than using boiling method.

EXAMPLE 10

Effects of Laser Power on Lysis Efficiency for Gram-negative Bacterial Cells

Figure 17:
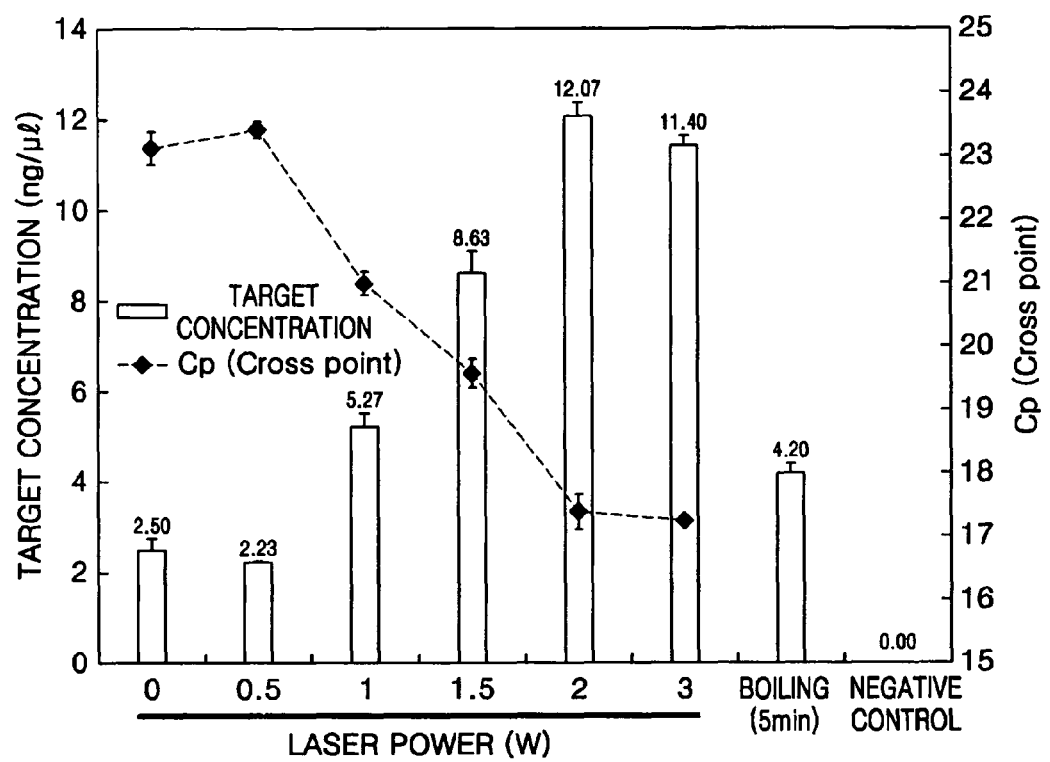
FIG. 17 is a graph illustrating PCR results of DNA released from $E.\ coli$ cells ($1\times10^5$ cells/µl) with respect to laser power.

To check the effects of laser radiation power on lysis efficiency for Gram-negative bacterial cells, laser radiation power of 0-3 W was used. The same experiment as in Example 9 was performed, except that *E. coli* cells ($1 \times 10^5$ cells/µl), which are Gram-negative bacterial cell, were used. FIG. 17 is a graph illustrating the PCR results of DNA released from *E. coli* cells ($1 \times 10^5$ cells/µl). In FIG. 17, Boiling (positive control) refers to the case when a PCR was performed on DNA released after boiling *E. coli* cells at 95° C. for 5 min; and Negative control refers to the case when a PCR was performed using only distilled water without DNA. The bars represent the concentration (ng/µl) of the amplified DNA. The amount of the PCR product was quantified by means of Agilent BioAnalyzer 2100. The error bars represent the standard deviation of the mean. As shown in FIG. 17, as laser radiation power increased, cell lysis efficiency increased. Specifically, the laser radiation power above 1 W was sufficient for the higher cell lysis efficiency than using the boiling method. In addition, as laser radiation power increases, the Cp value decreased, indicating that the amount of released DNA increased. But, the laser radiation power above 2W was saturated. This result suggests that starting target copy number increased as laser radiation power increased until all of cells were lyzed.

Thus, when cells or viruses are lyzed using the microchip of the present invention, laser radiation power can be significantly reduced.

To check the effects of the concentration of cells on cell lysis efficiency, the same experiment as described above carried out, except that *E. coli* cells ($1 \times 10^2$ cells/µl), which are Gram-negative bacterial cells, were used.

Figure 18:
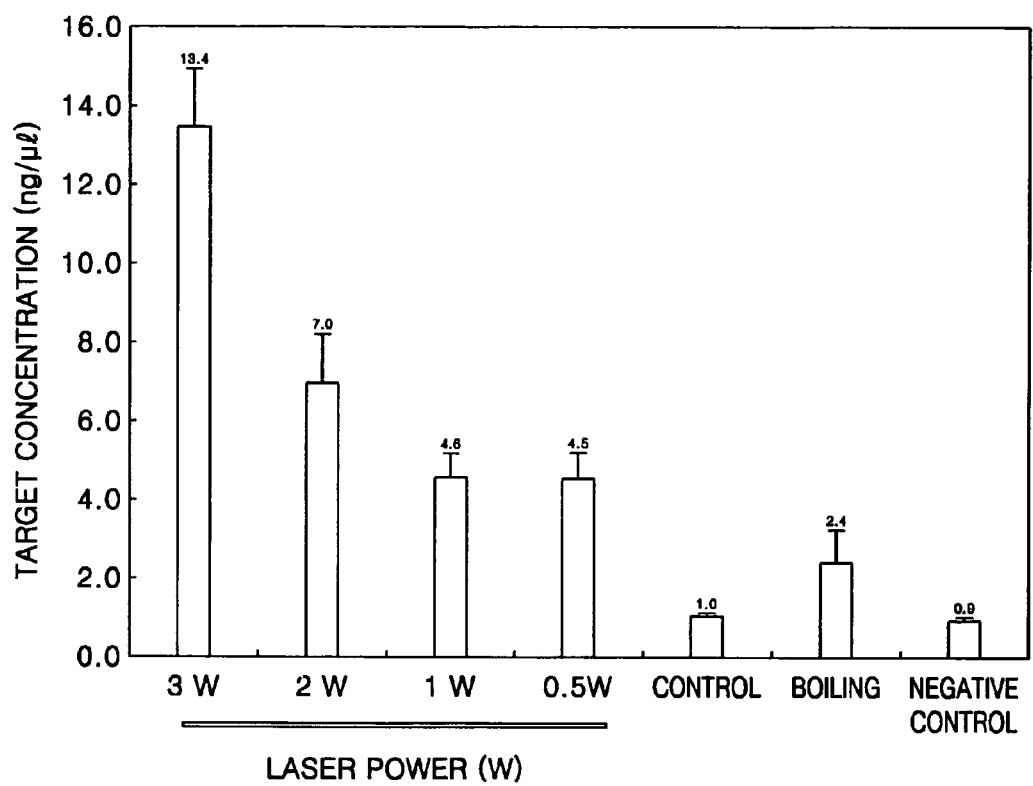
FIG. 18 is a graph illustrating PCR results of DNA released from $E.\ coli$ cells ($1\times10^2$ cells/µl) with respect to laser power.

FIG. 18 is a graph illustrating the PCR result of DNA released from *E. coli* cells ($1 \times 10^2$ cells/µl). In FIG. 18, Control refers to the case when a PCR was performed on supernatant obtained after centrifuging *E. coli* cells at 13,200 rpm for 5 min; Boiling (positive control) refers to the case when a PCR was performed on DNA released after boiling *E. coli* cells at 95° C. for 5 min; and Negative control refers to the case when a PCR was performed using only distilled water without DNA. The bars represent the concentration (ng/µl) of the amplified DNA. The amount of the PCR product was quantified by means of Agilent BioAnalyzer 2100. The error bars represent the standard deviation of the mean. As shown in FIG. 18, as laser radiation power increases, cell lysis efficiency increases. Specifically, the laser radiation power above 0.5 W was sufficient for the higher cell lysis efficiency than using the boiling method. The laser radiation power of 3 W provides much higher cell lysis efficiency than using the boiling method. Thus, when cells or viruses are lyzed using the microchip of the present invention, the laser radiation power can be significantly reduced.

Therefore, regardless of the concentration of cells, Gram-negative bacterial cells can be efficiently lyzed using the method of the present invention.

EXAMPLE 11

Effects of Laser Radiation Power on Temperature of *E. coli* Sample

Figure 19:
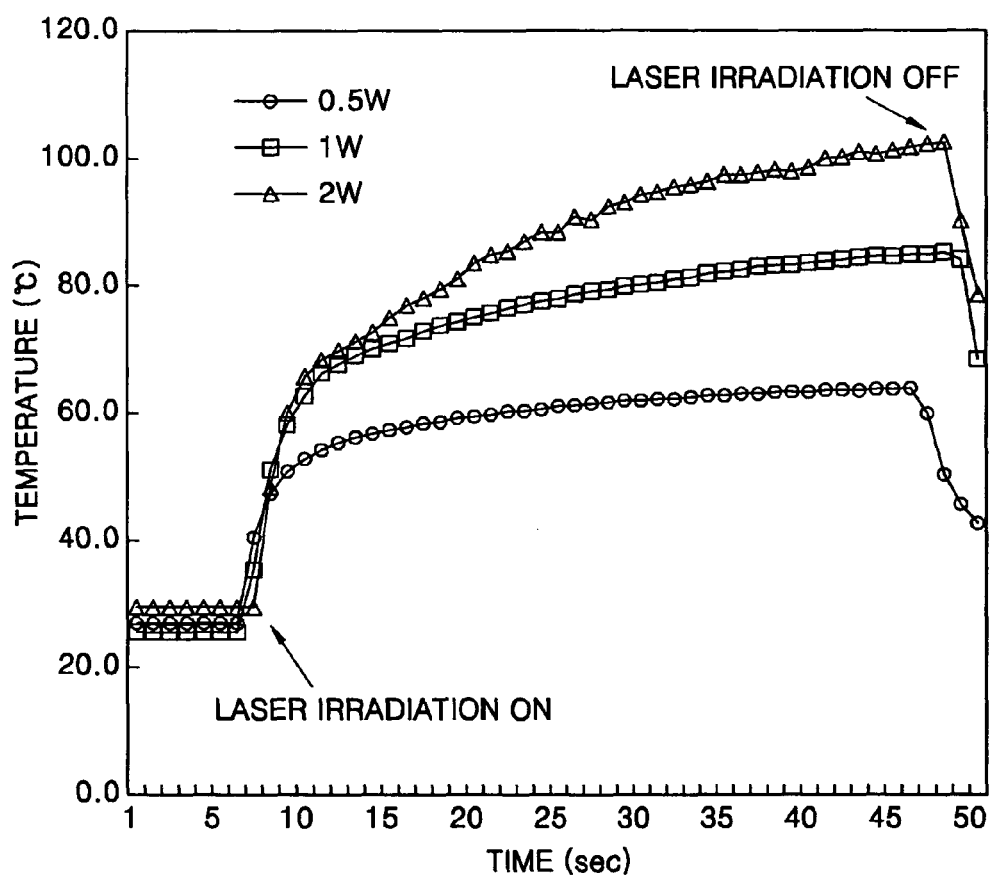
FIG. 19 is a graph illustrating the temperature of $E.\ coli$ sample with respect to laser power.

To check the effects of laser radiation power on the temperature of *E. coli* sample, laser radiation power of 0.5, 1, and 2 W were used. The same experiment as in Example 10 was carried out, except that *E. coli* cells ($1 \times 10^5$ cells/µl), which are Gram-negative bacterial cells, were used. FIG. 19 is a graph illustrating variation in temperature of *E. coli* sample with respect to laser radiation power. As shown in FIG. 19, the temperature of sample increased with the laser radiation power. In particular, after irradiating laser radiation power above 1 W for several seconds, the temperature of sample was rapidly raised above 65° C.

EXAMPLE 12

Effects of Surface Charge of Magnetic Beads and Material of Beads

Figure 20:
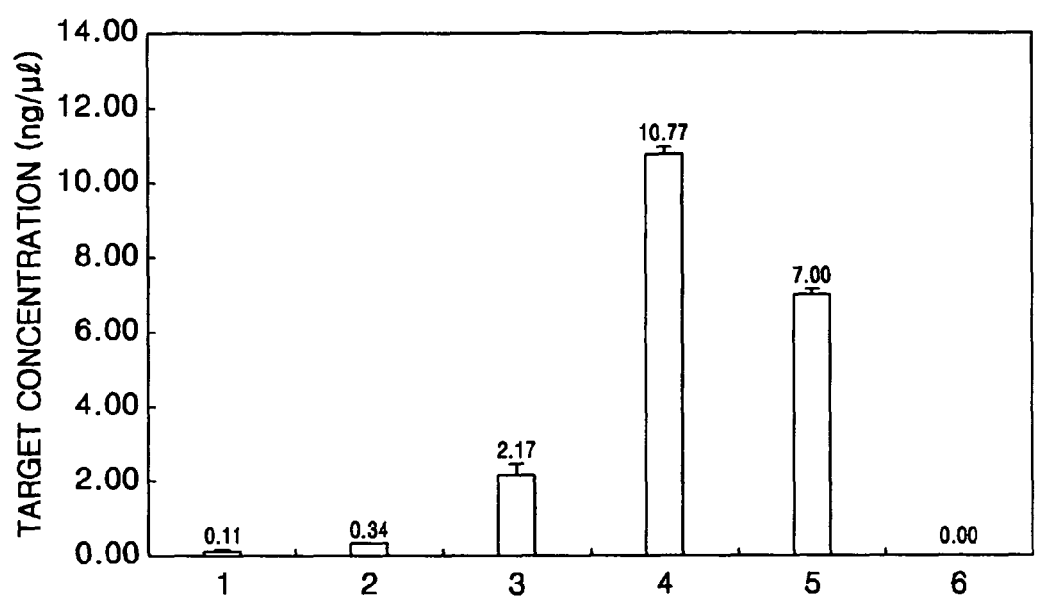
FIG. 20 is a graph illustrating PCR results of DNA released from $E.\ coli$ cells ($1\times10^5$ cells/µl) with respect to surface charge of magnetic beads and material of beads.

To check the effects of surface charge of magnetic beads and material of beads on cell lysis efficiency, four different types of beads were used. The same experiment as in Example 10 was carried out, except that the concentration of beads was 0.5%. FIG. 20 is a graph illustrating the PCR results of DNA released from *E. coli* cells ($1 \times 10^5$ cells/µl) with respect to surface charge of magnetic beads and material of beads. In FIG. 20, Samples 1, 2, 3, and 4 refer to the cases when a PCR was performed on DNA released using amine-terminated polystyrene magnetic beads, silica beads, polystyrene beads, and carboxylic acid-terminated polystyrene magnetic beads, respectively. Sample 5 (positive control) refers to the case when a PCR was performed on DNA released after boiling *E. coli* cells at 95° C. for 5 min and Sample 6 (negative control) refers to the case when a PCR was performed using only distilled water without DNA. The bars represent the concentration (ng/µl) of the amplified DNA. The amount of the PCR product was quantified by means of Agilent BioAnalyzer 2100. The error bars represent the standard deviation of the mean. As shown in FIG. 20, laser irradiation released *E. coli* DNA efficiently only in the presence of carboxylic acid terminated polystyrene magnetic beads.

In addition, the temperature of sample solution was investigated with four type microbeads (data not shown). Temperature of sample solution with silica beads was increased very slowly, because silica beads absorbed laser beams insufficiently with 1 W laser radiation power. Temperature of sample solution with amine-terminated polystyrene microbeads increased like carboxylic acid terminated polystyrene microbeads, but released DNA bind to microbeads because of the electrostatic interaction by the positive charge of amine functional group of the surface of the beads. Temperature of sample solution of polystyrene beads increased with middle speed between silica beads and magnetic beads, because of heat capacity of microbeads.

The greatest advantage of carboxylic acid terminated polystyrene magnetic beads is to reduce DNA isolation steps, because cell lysis using laser and micro magnetic beads lead to the denaturation and removal of proteins. Denatured proteins and cell debris stick to polystyrene surface of magnetic beads by adsorption, which facilitate easy removal by gravity or magnetic field. DNA does not bind to the beads because of the charge repulsion by the negative charge of carboxylic acid of the beads. This significantly improves PCR yield by lowering the limit of detection, reducing the time of DNA extraction, and increasing the signal amplitude.

EXAMPLE 13

Figure 21:
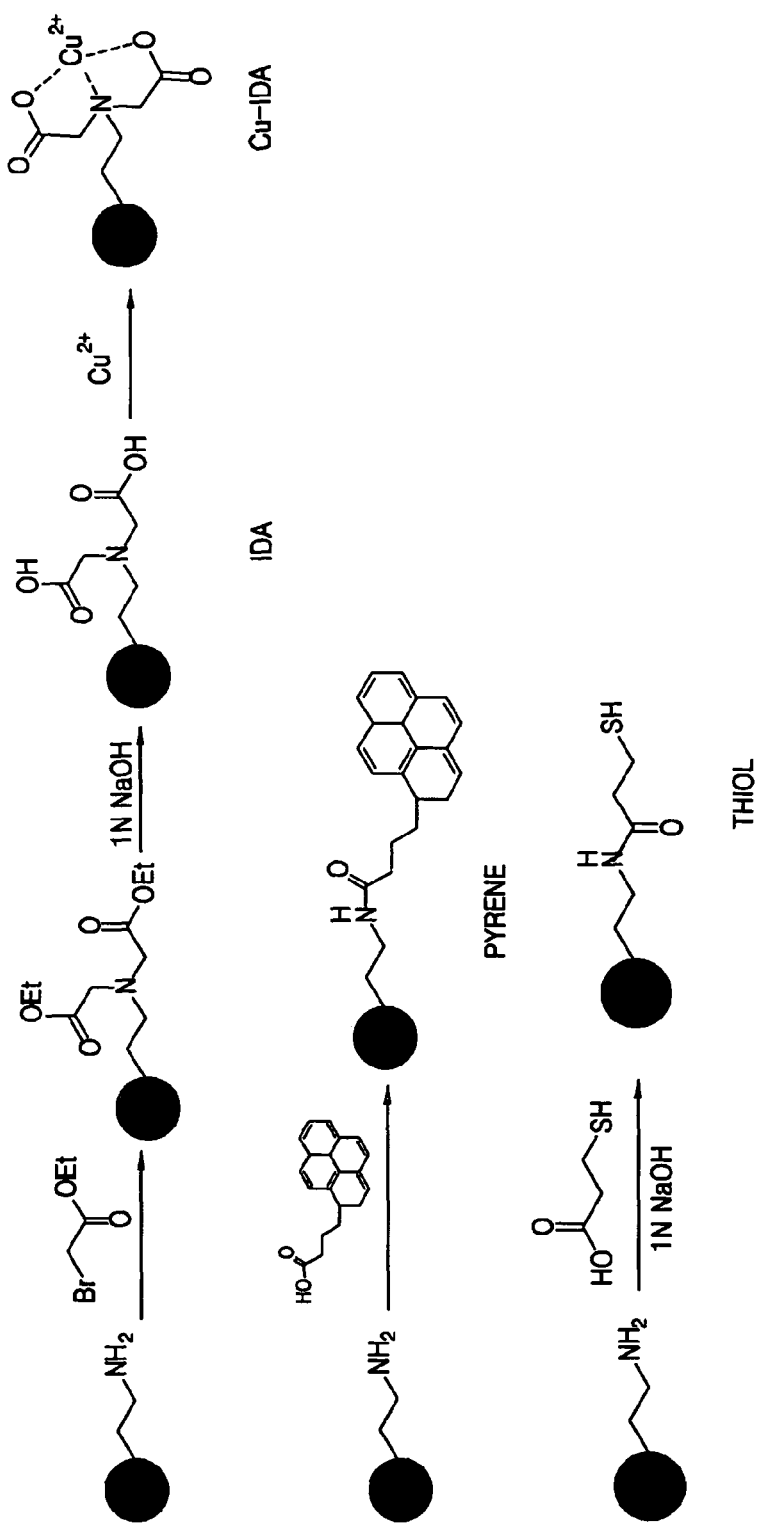
FIG. 21 illustrates a process of synthesizing iminodiacetic acid (IDA), Cu-IDA, pyrene, and thiol functional groups on the surface of a magnetic bead according to an embodiment of the present invention.

Effects of Functional Group of Magnetic Bead Surface on DNA Amplification Efficiency To check the effects of functional group of the surface of magnetic beads on cell lysis efficiency, the amplification efficiency of DNA released from cell lysis was investigated. First, various functional groups were synthesized on the surface of magnetic beads. FIG. 21 illustrates embodiments of synthesizing iminoacetic acid (IDA), pyrene, and thiol functional groups on the surface of magnetic beads. The process of synthesizing each functional group on magnetic beads (Dynabeads®) was as follows:

(1) IDA-Beads

500 µl of magnetic beads with amine functional group (Dynabeads®M-270 Amine, 30 mg/ml) was taken, and then the solution was removed using magnet. 500 µl of NMP (1-methyl-2-pyrrolidone) was sufficiently mixed with the beads, and then the solution was removed. This procedure was three times repeated. A solution of ethylbromoacetate (6 µl) and triethylamine (10 µl) in NMP (500 µl) was sufficiently mixed with the beads and left at 45° C. for 1 day. After the reaction was completed, the beads was washed with 500 µl of NMP (×3) and then with 500 µl of ethanol (×3). The solution was removed using magnet, and then 500 µl of a 1:1 (v/v) mixed solution of 1N NaOH and ethanol was added to the beads and left at room temperature for 1 hour. After the reaction was completed, the beads were washed with 500 µl of ethanol (×3), and then with 500 µl of tertiary distilled water (×3). Thereafter, the solution was removed and 500 µl of desired buffered solution was added thereto. The resultant was kept in cold storage.

(2) Cu-IDA-Beads

A solution of Cu(NO₃)₂ (100 mg) and TEA (100 µl) in NMP (500 µl) was added to IDA beads, and then the resultant was left for 1 day. After the reaction was completed, the beads were washed with 500 µl of NMP (×3), 500 µl of ethanol (×3), and tertiary distilled water (×3). Thereafter, the solution was removed and 500 µl of desired buffered solution was added thereto. The resultant was kept in cold storage.

(3) Pyrene-Beads

500 µl of magnetic beads with amine functional group (Dynabeads®M-270 Amine, 30 mg/ml) was taken, and then the solution was removed using magnet. 500 µl of NMP (1-methyl-2-pyrrolidone) was sufficiently mixed with the beads, and then the solution was removed. This procedure was three times repeated. A solution of 1-pyrenebutyric acid (15 mg), HBTU (o-benzotriazole-1-yl-N,N,N',N'-tetramethyluroniumhexafluorophosphate) (22 mg) and TEA (triethylamine) (7 µl) in NMP (500 µl) was sufficiently mixed with the beads and left at room temperature for 1 day. After the reaction was completed, the beads was washed with 500 µl of NMP (×3), 500 µl of ethanol (×3), and 500 µl of tertiary distilled water (×3). Thereafter, the solution was removed and 500 µl of desired buffered solution was added thereto. The resultant was kept in cold storage.

(4) Thiol-Beads

500 µl of magnetic beads with amine functional group (Dynabeads®M-270 Amine, 30 mg/ml) was taken, and then the solution was removed using magnet. 500 µl of NMP was sufficiently mixed with the beads, and then the solution was removed. This procedure was three times repeated. A solution of 3-mercaptopropionic acid (10 µl), HBTU (22 mg) and TEA (7 µl) in NMP (500 µl) was sufficiently mixed with the beads and left at room temperature for 1 day. After the reaction was completed, beads was washed with 500 µl of NMP (×3) and 500 µl of ethanol (×3). The solution was removed using magnet, and then 500 µl of a 1:1 (v/v) mixed solution of 1 N NaOH and ethanol was added to the beads and left at room temperature for 1 hour. After the reaction was completed, beads was washed with 500 µl of ethanol (×3) and 500 µl of tertiary distilled water (×3). Thereafter, the solution was removed and 500 µl of desired buffered solution was added thereto. The resultant was kept in cold storage.

Figure 22:
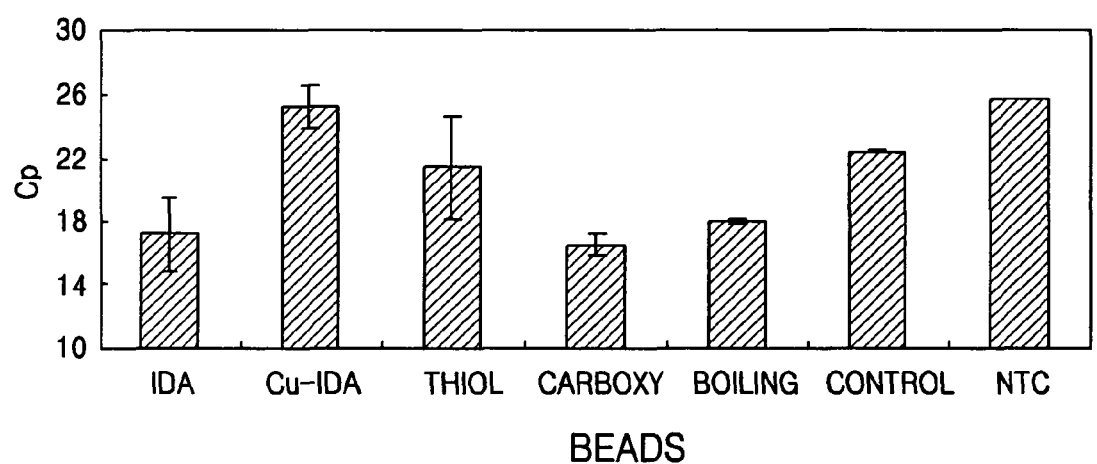
FIG. 22 is a graph illustrating the PCR results [crossing point (Cp)] of DNA released from $E.\ coli$ cells with respect to functional groups on the surface of magnetic beads.

DNA amplification efficiency was investigated using the magnetic beads on which each functional group was synthesized. The same experiment as in Example 12 was carried out, except that $E.\ coli$ cells ($1 \times 10^7$ cells/µl) were used. FIG. 22 is a graph illustrating the PCR results (Cp) of DNA released from $E.\ coli$ cells with respect to functional group of the surface of magnetic beads. In FIG. 22, Carboxy bead refers to the case when a PCR was performed after lyzing cells using Dynabeads® MyOne™ Carboxylic Acid (DYNAL, Norway); Boiling (positive control) refers to the case when a PCR was performed on DNA released after boiling $E.\ coli$ cells at 95° C. for 5 min; Control refers to the case when a PCR was performed on supernatant after centrifuging $E.\ coli$ cells at 13,200 rpm for 5 min; and Negative control (NTC) refers to the case when a PCR was performed using only distilled water without DNA. As shown in FIG. 22, IDA among functional groups had the lowest Cp value and the Cp value of thiol was smaller than the Cp value of Cu-IDA. Further, as the hydrophilicity of the functional group increased, the Cp value decreased. That is, IDA had lower Cp value than thiol. It can be seen from above results that the beads with carboxy functional group, which is hydrophilic, have best cell lysis efficiency and the Cu-IDA beads with blocked functional group have low cell lysis efficiency.

EXAMPLE 14

Figure 23:
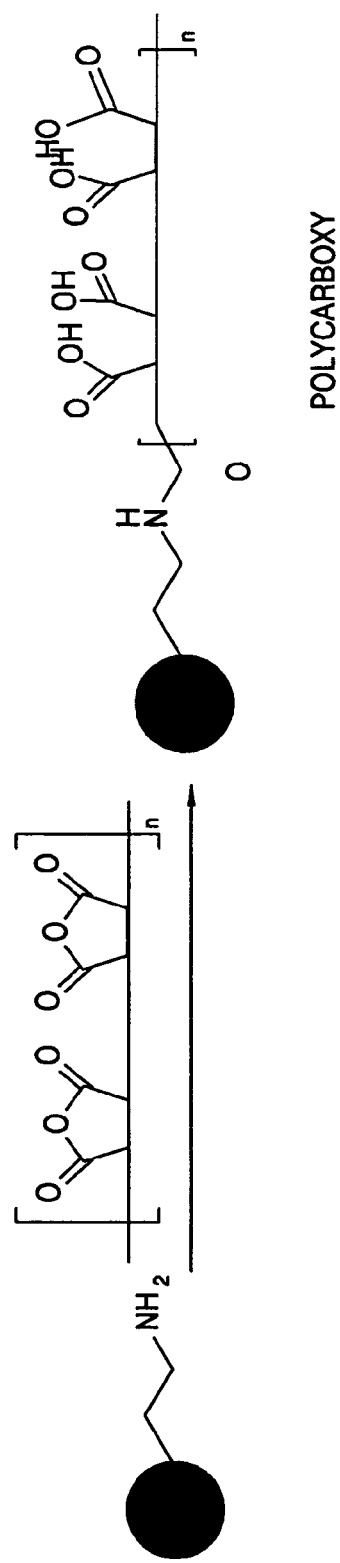
FIG. 23 illustrates an embodiment of synthesizing a polycarboxy functional group on the surface of a magnetic bead.

Effects of pH of Solution Containing Magnetic Beads on DNA Amplification Efficiency To check the effects of pH of a solution containing magnetic beads on DNA amplification efficiency, three types of beads, i.e., magnetic beads with carboxy (Dynabeads®), magnetic beads with IDA, and polycarboxy magnetic beads were used. Since in the experimental results described above, beads with carboxy functional group had the highest cell lysis efficiency, polycarboxy beads having many carboxy functional groups were synthesized. FIG. 23 illustrates a process of synthesizing polycarboxy functional group on the surface of a magnetic bead. The process of synthesizing said functional group on magnetic beads (Dynabeads®) was as follows:

500 µl of magnetic beads with amine functional group (Dynabeads®M-270 Amine, 30 mg/ml) was taken, and then the solution was removed using magnet. 500 µl of NMP was sufficiently mixed with the beads, and then the solution was removed. This procedure was three times repeated. A solution of poly(ethylene-alt-maleic anhydride) (100 mg) and triethylamine (10 μl) in NMP (500 μl) was sufficiently mixed with the beads and left at room temperature for 1 day. After the reaction was completed, beads was washed with 500 μl of NMP (×3) and then with 500 μl of ethanol (×3). The solution was removed using magnet, and then 500 μl of a 100 mM Tris-HCl buffered solution (pH 9.0) was added to the beads and left at room temperature for 1 hour. After the reaction was completed, the beads were washed with 500 μl of ethanol (×3), and then with 500 μl of tertiary distilled water (×3). Thereafter, the solution was removed and 500 μl of desired buffered solution was added thereto. The resultant was kept in cold storage.

Figure 24:
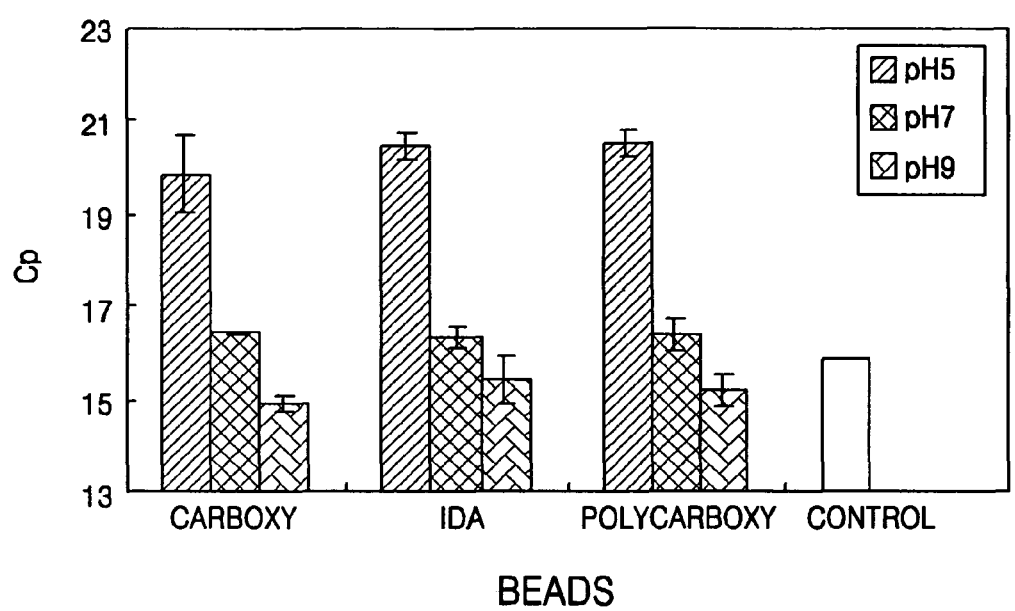
FIG. 24 is a graph illustrating the PCR results (Cp) of DNA released from $E.\ coli$ cells with respect to functional groups on the surface of magnetic beads and pH of a bead solution.

The same experiment as in Example 13 was carried out, except that the three types of beads were adjusted to pH 5, 7 and 9. FIG. 24 is a graph illustrating the PCR results (Cp) of DNA released from *E. coli* cells with respect to functional group on the surface of magnetic beads and pH of bead solutions. In FIG. 24, Control refers to the case when a PCR was performed after lyzing cells using Dynabeads® MyOne™ Carboxylic Acid (DYNAL, Norway). As shown in FIG. 24, the Cp value decreased as pH increased. Thus, It can be seen that the cell lysis efficiency increases with the pH of the solution containing magnetic beads. However, at the same pH, the cell lysis efficiency is not significantly changed due to functional group.

EXAMPLE 15

Comparison of PCR Efficiency in the Presence of Inhibitor

In Examples 13 and 14, when pure *E. coli* cells were used, the cell lysis efficiency depended on the pH of the solution containing magnetic beads. When the surface functional group is a carboxy group, the cell lysis efficiency is not significantly varied due to the structure thereof. This is because when only pure *E. coli* cells are used, the inhibition effects of cell debris on a PCR are insignificant. Therefore, to check the effects of functional group of the surface of beads on the removal of a PCR inhibitor, cell lysis efficiency according to the type of magnetic beads and pH was compared.

Figure 25:
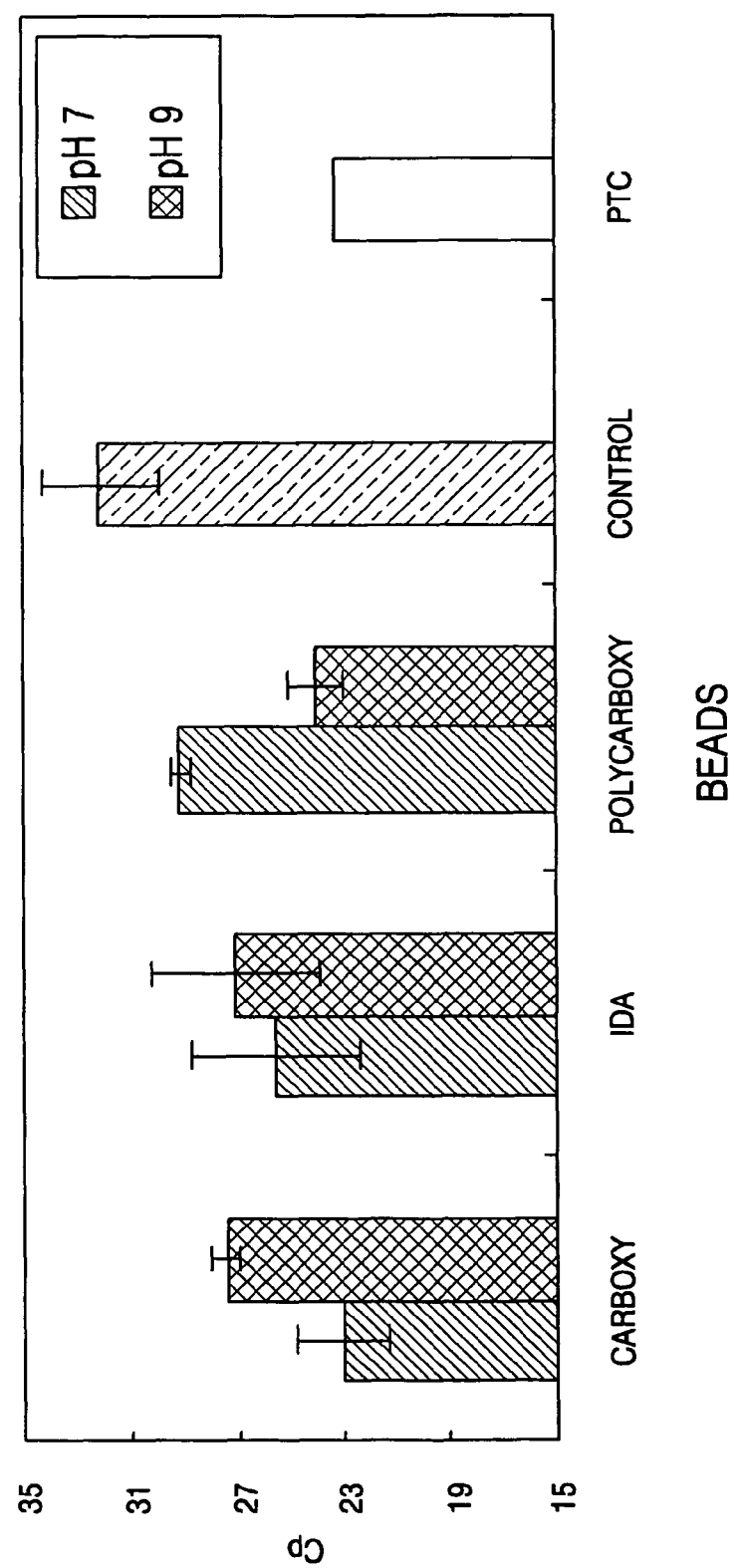
FIG. 25 is a graph illustrating the PCR results (Cp) of DNA released from $E.\ coli$ cells with respect to functional groups on the surface of magnetic beads in the presence of 10% serum.

First, the same experiment as in Example 14 was carried out, except that 10% serum was added as an inhibitor and the pH of a solution containing magnetic beads was adjusted to 7 and 9. FIG. 25 is a graph illustrating the PCR results (Cp) of DNA released from *E. coli* cells with respect to functional group of the surface of magnetic beads in the presence of 10% serum. In FIG. 25, Control refers to the case when a PCR was performed after lyzing cells using Dynabeads® MyOne™ Carboxylic Acid (DYNAL, Norway) in the presence of 10% serum; and PTC (positive control) refers to the case when a PCR was performed after adding 10% serum to DNA released from *E. coli*. As shown in FIG. 25, the Cp values of magnetic beads having the same functional group varied depending on pH. That is, carboxy and IDA had a lower Cp value at pH 7 than at pH 9 and polycarboxy had a lower Cp value at pH 9 than at pH 7. Thus, it can be seen that when a carboxy functional group and the pH of the solution containing magnetic beads are properly combined, the effects of an inhibitor on a PCR can be significantly reduced.

Figure 26:
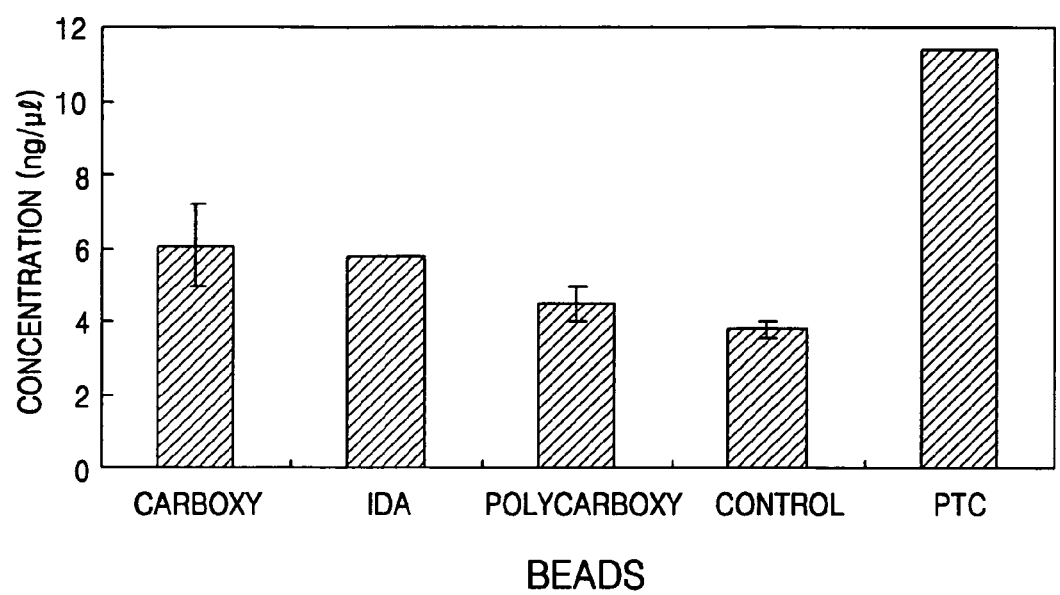
FIG. 26 is a graph illustrating the PCR results (the concentration of PCR product) of DNA released from Hepatitis B virus (HBV) with respect to functional groups on the surface of magnetic beads in the presence of 10% serum.

Next, the same experiment as described above was carried out, except that Hepatitis B virus (HBV) was used instead of *E. coli* and the pH of a solution containing magnetic beads was adjusted to 7. The following pair of primer was used for PCR: forward primer; reverse primer. This pair of primer is a site corresponding to a core region of HBV genome. FIG. 26 is a graph illustrating the PCR results (concentration of PCR product) of DNA released from HBV with respect to functional group of the surface of magnetic beads in the presence of 10% serum. In FIG. 26, Control refers to the case when a PCR was performed after lyzing HBV using Dynabeads® MyOne™ Carboxylic Acid (DYNAL, Norway) in the presence of 10% serum; and PTC (positive control) refers to the case when a PCR was performed on DNA isolated from HBV without 10% serum. As shown in FIG. 26, the PCR product was also generated even in the presence of 10% serum. Thus, when the carboxy functional group and the pH of the solution containing magnetic beads are properly combined, the effects of an inhibitor on PCR can be significantly reduced.

EXAMPLE 16

Investigation of Cell Viability According to Laser Irradiation

Figure 27:
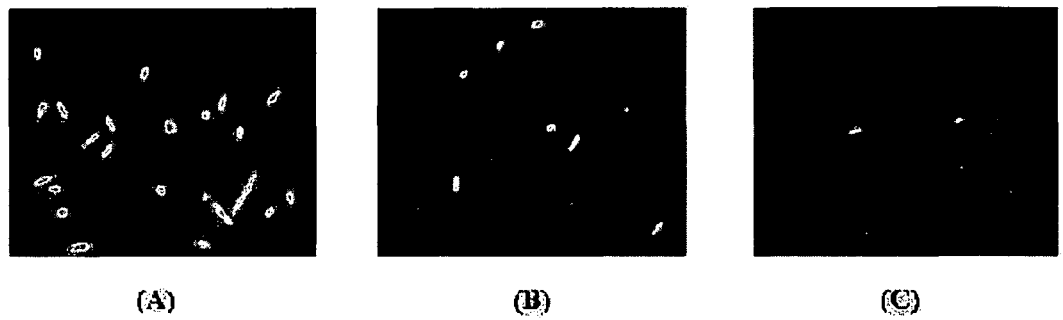
FIG. 27 is a photograph illustrating viability of $E.\ coli$ cells with respect to laser irradiation.

To observe live and dead cells present in a sample solution according to laser irradiation, *E. coli* cells were used. FIG. 27 is a photograph showing the viability of *E. coli* cells according to laser irradiation. In FIG. 27, Panel A is an image of *E. coli* cells without micro magnetic beads before the laser irradiation; Panel B is an image of *E. Coli* cells in the presence of micro magnetic beads after the laser irradiation for 40 sec at 808 nm with 0.5 W laser radiation power; and Panel C is an image of *E. coli* cells in the presence of micro magnetic beads after the laser irradiation for 40 sec at 808 nm with 1 W laser radiation power. Green-stained cells are live cells and red-stained cells are dead cells. As shown in FIG. 27, most cells are alive before the laser irradiation and the proportion of dead cells increases with laser radiation power.

EXAMPLE 17

Effects of Laser Irradiation on Damage of Genomic DNA

Figure 28:
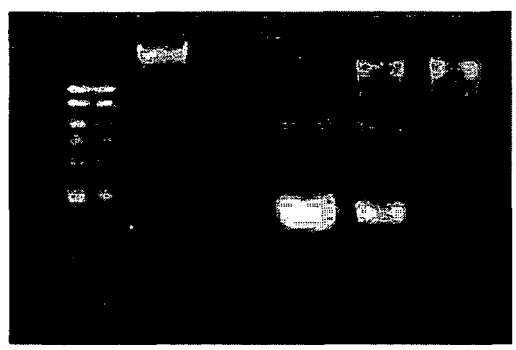
FIG. 28 is a photograph of DNA analysis after laser irradiation to an $E.\ coli$ BL21 cell harbouring pCR®II-TOPO® (Invitrogen) plasmid.

To check whether the laser irradiation damages genomic DNA, it was checked whether the isolated DNAs are sheared after 40 sec irradiation with laser. FIG. 28 is a photograph of DNA analysis after laser irradiation on an *E. coli* BL21 cell harbouring pCR®II-TOPO® (Invitrogen) plasmid. In FIG. 28, Lane 1 refers to the case when DNA was isolated using the method of the present invention; Lane 2 refers to the case when DNA was isolated after boiling at 95° C. for 5 min; Lane 3 refers to the case when plasmid DNA was isolated using Qiagen QIAprep® miniprep kit; Lane 4 refers to the case when genomic DNA of BL21 was isolated using Qiagen QIAamp® DNA minikit; and Lane 5 refers to the case when genomic DNA of BL21 was isolated from *E. coli* BL21 cells without the plasmid using Qiagen QIAamp® DNA mini kit. Lane 5 was used to identify the correct band for genomic DNA. As shown in FIG. 28, there was no damage on DNA. As expected, with QIAprep Mini kit (Qiagen) for plasmid preparation, there was little contamination with the genomic DNA (Lane 3). Interestingly, with the method of the present invention, genomic DNA was preferentially isolated with much less contamination with plasmid DNA. In contrast, with QIAamp Mini kit for the genomic DNA isolation that uses silica-gel-membrane technology after proteinase K treatment to the bacteria, there was a lot of plasmid DNA contamination (Lane 4). This might explain why better yield for PCR amplification with DNA isolated by the method of the present invention than with DNA isolated by Qiagen kit could be obtained.

In the present invention, a novel method for efficient cell lysis have been developed by combining laser and micromagnetic beads; micro magnetic-beads present in cell suspension caused rapid cell lysis when laser beam was applied to this sample, allowing bacterial cells to be disrupted in a few seconds. Most importantly, DNAs released from cells disrupted this way was far more efficiently amplified by PCR than those from cells lyzed by other two conventional means, indicating that the release of a substance(s) during cell lysis that interferes with amplification of DNA is minimal compared to other methods. The easiness, efficient cell lysis and release of DNA render a new cell lysis method well-suited to be integrated into LOC application.

As described above, according to the method of the present invention, rapid cell lysis within 40 seconds is possible, an apparatus for the disruption of cells or viruses can be miniaturized using a laser diode, a DNA purification step can be directly performed after a disruption of cells or viruses, and a solution containing DNA can be transferred to a subsequent step after cell debris and magnetic beads to which inhibitors of a subsequent reaction are attached are removed with an electromagnet. In addition, by means of the cell lysis chip of the present invention, an evaporation problem is solved, vibrations can be efficiently transferred to cells through magnetic beads, a microfluidics problem on a rough surface is solved by hydrophobically treating the inner surface of the chip, and the cell lysis chip can be applied to LOC.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. An apparatus for disruption of cells or viruses comprising:
 a cell lysis chamber formed in a microchip, the microchip comprising:
  a chip body having a top surface and a bottom surface, and including a cut-out defining the cell lysis chamber opened to the top surface and to the bottom surface of the chip body;
  a chip cover attached to the top surface of the chip body to close the top surface of the cell lysis chamber, wherein the chip cover is made of a material withstanding a high temperature and which has a transmittance for a laser of at least 90%, and has an inlet hole and an outlet hole to the cell lysis chamber;
  a chip bottom attached to the bottom surface of the chip body to close the bottom surface of the cell lysis chamber; and
  a chip bonding part for attaching the chip bottom to the bottom surface of the chip body;
 beads included in the cell lysis chamber, and coated with one or more hydrophilic and negatively charged groups;
 a member for receiving the cell lysis microchip; and
 a laser generator for supplying the laser to the cell lysis chamber.

2. The apparatus of claim 1, the member further comprising a DNA purification chamber connecting to the cell lysis chamber through a channel or
a DNA amplification chamber connecting to the cell lysis chamber through a channel.

3. The apparatus of claim 1, wherein the beads are magnetic beads.

4. The apparatus of claim 3, further comprising
 an electromagnet for removing the magnetic beads in the cell lysis chamber.

5. The apparatus of claim 1, wherein the laser is a pulse laser having a power of 1mJ/pulse or more or a continuous wave (CW) laser having a power of 10 mW or more.

6. The apparatus of claim 1, wherein the laser is generated in a wavelength range of 400 nm or more.

7. The apparatus of claim 1, wherein the chip body is made of silicon, glass, or a polymer.

8. The apparatus of claim 1, wherein the chip cover is made of glass, a polymer, or indium tin oxide glass.

9. The apparatus of claim 1, wherein the chip bottom is made of glass, silicon, a polymer, or indium tin oxide glass.

10. The apparatus of claim 1, wherein the chip bonding part is an adhesive tape or an adhesive.

11. The apparatus of claim 1, wherein the chip cover is made of glass, the chip body is made of silicon, the chip bottom is made of polycarbonate film, and the chip bonding part is a double-coated adhesive tape.

12. The apparatus of claim 1, further comprising
an anti-evaporation part for sealing the inlet hole and the outlet hole of the microchip.

13. The apparatus of claim 12, further comprising
a vibrator and a vibration transfer part, wherein the vibrator contacts the vibration transfer part and the vibration transfer part contacts the chip bottom.

14. The apparatus of claim 1, wherein the beads are coated with iminodiacetic acid, ethylene diaminetetraacetic acid, citric acid, or polycarboxylic acid.

* * * * *

SEQUENCE LISTING

```
<160> NUMBER OF SEQ ID NOS: 2

<210> SEQ ID NO 1
<211> LENGTH: 20
<212> TYPE: DNA
<213> ORGANISM: artificial sequence
<220> FEATURE:
<223> OTHER INFORMATION: primer

<400> SEQUENCE: 1
cccagactcc tacgcgaggc                                              20

<210> SEQ ID NO 2
<211> LENGTH: 22
<212> TYPE: DNA
<213> ORGANISM: artificial sequence
<220> FEATURE:
<223> OTHER INFORMATION: primer

<400> SEQUENCE: 2
gtattaccgc aactgctggc ac                                           22
```